(12) United States Patent
Fevig et al.

(10) Patent No.: US 7,723,355 B2
(45) Date of Patent: May 25, 2010

(54) 7,8-DIHYDRO-1,6-NAPHTHYRIDIN-5(6H)-ONES AND RELATED BICYCLIC COMPOUNDS AS INHIBITORS OF DIPEPTIDYL PEPTIDASE IV AND METHODS

(75) Inventors: John M. Fevig, Doylestown, PA (US); Jianxin Feng, Mechanicville, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 202 days.

(21) Appl. No.: 11/941,181

(22) Filed: Nov. 16, 2007

(65) Prior Publication Data

US 2009/0149492 A1    Jun. 11, 2009

Related U.S. Application Data

(60) Provisional application No. 60/860,202, filed on Nov. 20, 2006.

(51) Int. Cl.
*A61K 31/4375* (2006.01)
*C07D 471/04* (2006.01)
*A61P 3/10* (2006.01)

(52) U.S. Cl. ...................... 514/300; 546/122
(58) Field of Classification Search ................ 546/122; 514/300
See application file for complete search history.

(56) References Cited

FOREIGN PATENT DOCUMENTS

| WO | WO2004/014866 | * | 2/2004 |
|----|---------------|---|--------|
| WO | WO2004/014893 | * | 2/2004 |
| WO | WO2005/123685 |   | 12/2005 |
| WO | WO2006/019965 |   | 2/2006 |
| WO | 2006032470    | * | 3/2006 |
| WO | WO2006/065842 | * | 6/2006 |

OTHER PUBLICATIONS

Bandhari, A. et al., "Solid-Phase Synthesis of Pyrrolo[3,4-b]pyridines and related pyridine-fused Heterocycles", Synthesis, No. 11, pp. 1951-1960, 1999.
Yamada, M. et al., "A Potent Dipeptide Inhibitor of Dipeptidyl Peptidase", Bioorganic and Medicinal Chemistry Letters, vol. 8, pp. 1537-1540, 1998.

* cited by examiner

*Primary Examiner*—D. Margaret Seaman
*Assistant Examiner*—Niloofar Rahmani
(74) *Attorney, Agent, or Firm*—Burton Rodney; Maureen S. Gibbons

(57) ABSTRACT

The present application provides compounds, including all stereoisomers, solvates, prodrugs and pharmaceutically acceptable forms thereof according to Formula I. Additionally, the present application provides pharmaceutical compositions containing at least one compound according to Formula I and optionally at least one additional therapeutic agent. Finally, the present application provides methods for treating a patient suffering from an DPP4 modulated disease or disorder such as, for example, diabetes, by administration of a therapeutically effective dose of a compound according to Formula I.

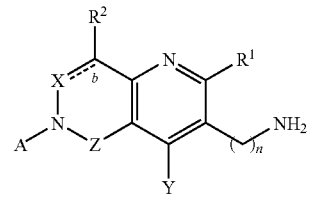

I wherein X, Z, A, $R^2$, Y, $R^1$, n, and b are as defined herein.

13 Claims, No Drawings

7,8-DIHYDRO-1,6-NAPHTHYRIDIN-5(6H)-ONES AND RELATED BICYCLIC COMPOUNDS AS INHIBITORS OF DIPEPTIDYL PEPTIDASE IV AND METHODS

FIELD OF THE INVENTION

The present invention relates to 7,8-dihydro-1,6-naphthyridin-5(6H)-ones and related bicyclic compounds which are inhibitors of dipeptidyl peptidase IV (DPP-4), and to a method for treating diabetes and related diseases or disorders by employing such compounds alone, or in combination with another type of therapeutic agent.

BACKGROUND OF THE INVENTION

Dipeptidyl peptidase IV (DPP-4) is a membrane bound non-classical serine aminodipeptidase which is located in a variety of tissues (intestine, liver, lung, kidney) as well as on circulating T-lymphocytes (where the enzyme is known as CD-26). It is responsible for the metabolic cleavage of certain endogenous peptides (GLP-1(7-36), glucagon) in vivo and has demonstrated proteolytic activity against a variety of other peptides (GHRH, NPY, GLP-2, VIP) in vitro.

GLP-1(7-36) is a 30 amino-acid peptide derived by post-translational processing of proglucagon in the small intestine. GLP-1(7-36) has multiple actions in vivo including the stimulation of insulin secretion, inhibition of glucagon secretion, the promotion of satiety, and the slowing of gastric emptying. Based on its physiological profile, the actions of GLP-1(7-36) are expected to be beneficial in the prevention and treatment of Type II diabetes and potentially obesity. To support this claim, exogenous administration of GLP-1(7-36) (continuous infusion) in diabetic patients has demonstrated efficacy in this patient population. Unfortunately GLP-1(7-36) is degraded rapidly in vivo and has been shown to have a short half-life in vivo ($t^{1/2} \approx 1.5$ min). Based on a study of genetically bred DPP-4 KO mice and on in vivo/in vitro studies with selective DPP-4 inhibitors, DPP-4 has been shown to be the primary degrading enzyme of GLP-1(7-36) in vivo. GLP-1(7-36) is degraded by DPP-4 efficiently to GLP-1(9-36), which has been speculated to act as a physiological antagonist to GLP-1(7-36). Thus, inhibition of DPP-4 in vivo should potentiate endogenous levels of GLP-1(7-36) and attenuate formation of its antagonist GLP-1(9-36) and thus serve to ameliorate the diabetic condition.

DETAILED DESCRIPTION OF THE INVENTION

In accordance with the present invention, compounds of formula (I) are provided

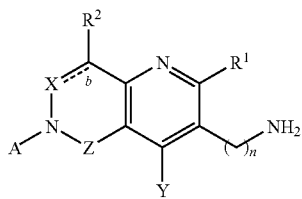

I wherein
b is a single or double bond;
n is 1 or 2;
$R^1$ is selected from the group consisting of hydrogen (H), halogen, $CF_3$, cyano (CN), amino, substituted amino, alkyl, alkenyl, alkynyl, cycloalkyl, cycloalkylalkyl, bicycloalkyl, cycloalkenyl, aryl, heteroaryl, and cycloheteroalkyl, wherein any such functional group may optionally be substituted with 1 to 3 or more substituents selected from the group consisting of hydrogen, halo, alkyl, polyhaloalkyl, alkoxy, aryl, haloalkoxy, polyhaloalkoxy, alkoxycarbonyl, alkenyl, alkynyl, cycloalkyl, bicycloalkyl, cycloalkylalkyl, polycycloalkyl, heteroarylamino, arylamino, cycloheteroalkyl, heteroaryl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, arylalkylthio, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl;

X is selected from the group consisting of C=O, C=S, $CHR^3$, or $CR^3$;

$R^2$ and $R^3$ are independently selected from the group consisting of hydrogen, alkyl and aryl;

Z is selected from the group consisting of C=O, C=S, and $CHR^4$;

$R^4$ is selected from the group consisting of hydrogen, alkyl and aryl;

A is selected from the group consisting of hydrogen (H), alkyl, alkenyl, alkynyl, cycloalkyl, bicycloalkyl, cycloalkenyl, aryl, heteroaryl, cycloheteroalkyl, O—$R_1$, cyano, amino, —C(O)—OH, —C(O)—$NR^6R^7$, —C(O)—$OR^6$, $S(O)_m$—$R^6$, —$S(O)_2NR^6R^7$, —$NR^6R^7$, —$NR^6$—C(O)$R^7$ and —$NR^6$—$SO_2R^7$, wherein any such functional group may optionally be substituted with one to three or more substituents selected from the group consisting of hydrogen, halo, alkyl, polyhaloalkyl, alkoxy, aryl, haloalkoxy, polyhaloalkoxy, alkoxycarbonyl, alkenyl, alkynyl, cycloalkyl, bicycloalkyl, cycloalkylalkyl, polycycloalkyl, heteroarylamino, arylamino, cycloheteroalkyl, heteroaryl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, arylalkylthio, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl;

m is 0, 1 or 2;

$R_1$ is selected from the group consisting of hydrogen, alkyl, and aryl;

$R^6$ and $R^7$ are
(i) each independently selected from the group consisting of hydrogen (H), alkyl, alkenyl, alkynyl, cycloalkyl, bicycloalkyl, alkylthioalkyl, arylalkylthioalkyl, cycloalkenyl, aryl, heteroaryl, heteroarylalkyl, and cycloheteroalkyl, wherein either functional group may optionally be substituted with one to three or more substituents selected from the group consisting of hydrogen, halo, alkyl, polyhaloalkyl, alkoxy, aryl, haloalkoxy, polyhaloalkoxy, alkoxycarbonyl, alkenyl, alkynyl, cycloalkyl, bicycloalkyl, cycloalkylalkyl, polycycloalkyl, heteroarylamino, arylamino, cycloheteroalkyl, heteroaryl, cycloheteroalkylalkyl, hydroxy, hydroxyalkyl, nitro, cyano, amino, substituted amino, alkylamino, dialkylamino, thiol, alkylthio, arylalkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl; or (ii) $R^6$ and $R^7$ in $NR^6R^7$ may be taken together to form a 5- or 6-membered saturated or partially unsaturated ring system selected from the group consisting of cycloheteroalkyl and heteroaryl; wherein such ring system may optionally be substituted with one to three or more substituents selected from the group consisting of hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl; and Y is selected from the group consisting of aryl and heteroaryl, wherein said aryl or heteroaryl may optionally be substituted with one to three or more substituents selected from the group consisting of hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl.

The definition of formula I above includes all pharmaceutically acceptable salts, stereoisomers, and prodrug esters of formula I.

The compounds of formula I possess activity as inhibitors of DPP-4 in vivo and are useful in the treatment of diabetes, especially Type II diabetes, and the micro- and macrovascular complications of diabetes such as retinopathy, neuropathy, nephropathy, and wound healing. Such diseases and maladies are also sometimes referred to as "diabetic complications".

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

Further provided is a method for treating or delaying the progression or onset of diabetes, especially Type II diabetes, including complications of diabetes, including retinopathy, neuropathy, nephropathy and delayed wound healing, and related diseases such as insulin resistance (impaired glucose homeostasis), hyperglycemia, hyperinsulinemia, elevated blood levels of fatty acids or glycerol, obesity, hyperlipidemia including hypertriglyceridemia, Syndrome X, atherosclerosis and hypertension, and for increasing high density lipoprotein levels, wherein a therapeutically effective amount of a compound of formula I is administered to a mammalian, e.g., human, patient in need of treatment.

The compounds of the invention can be used alone, in combination with other compounds of the present invention, or in combination with one or more other agent(s) active in the therapeutic areas described herein.

In addition, a method is provided for treating diabetes, especially Type II diabetes, and related diseases as defined above and hereinafter, wherein a therapeutically effective amount of a combination of a compound of formula I and at least one other type of therapeutic agent, such as an antidiabetic agent and/or a hypolipidemic agent, is administered to a human patient in need of treatment.

Preferred are compounds of formula I wherein b represents a single bond;

n is 1;

$R^1$ is alkyl;

X is $CHR^3$ or $C=O$;

$R^2$ is H;

Z is $C=O$;

Y is aryl;

A is H, alkylcarbonylalkyl, aminocarbonylalkyl, alkylaminocarbonylalkyl, dialkylaminocarbonylalkyl, heterocyclocarbonylalkyl, alkyl, alkoxyalkyl, hydroxyalkyl, aryl, or alkoxyaryl.

Still more preferred are compounds of formula I where b is a single bond;

$R^1$ is methyl;

X is $CH_2$ or $C=O$;

$R^2$ is H;

Z is $C=O$;

Y is phenyl, halophenyl, or dihalophenyl;

A is H, i-propylcarbonylmethyl, aminocarbonylmethyl, methylaminocarbonylmethyl, diethylaminocarbonylmethyl, pyrrolidino-carbonylmethyl, piperidinocarbonyl, 2-oxo-1,4'-bipiperidinylcarbonylmethyl, morpholinylcarbonylmethyl, methyl, tetrahydrofuranylmethyl, methoxyethyl, hydroxyethyl, phenyl, or methoxyphenyl.

Most preferred are compounds of formula I where

Z is $C=O$;

X is $CHR^{3a}$, where $R^3$ is H;

X is $C=O$;

b is a single bond;

$R^2$ is H;

$R^1$ is $CH_3$;

n is 1;

Y is

[structure: dichlorophenyl group with two Cl substituents]; and

A is

[structure: (CH3)2N-C(=O)-CH2- group]

-continued

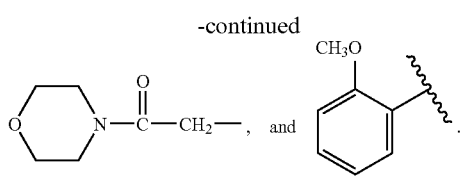

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of formula I falling into a given class may be compatible with some of the reaction conditions required in some of the methods described. Such restrictions to the substituents, which are compatible with the reaction conditions, will be readily apparent to one skilled in the art and alternate methods must be used.

Scheme 1 provides a general route to prepare aminomethyl 7,8-dihydro-1,6-naphthyridin-5(6H)-ones of formula IA of the invention, where n is 1, Z is —C=O, X is $CH_2$ and b is a single bond. A chloroketone of formula (I) (where $R^a$ is alkyl), obtained from commercial sources, is condensed with aldehyde (2) under a variety of conditions, such as under mild acidic catalysis, to form the conjugated ester (3). One preferred set of conditions involves reacting (1) and (2) in an alcoholic solvent, such as isopropanol, at ambient or elevated temperature, in the presence of benzylamine and acetic acid. Condensation of (3) with enamine (4) (where $R^b$ is alkyl) in an alcoholic solvent such as isopropanol, yields a dihydropyridine of formula (5).

Enamines of formula (4) can be obtained from commercial sources or can be prepared by reaction of the corresponding acetoacetate with ammonia. In some cases, the dihydropyridines (5) can be conveniently prepared in one pot by addition of enamine (4) directly to the reaction mixture in which (1) and (2) are condensed to give (3). Oxidation of dihydropyridine (5) to pyridine (6) can be performed by a variety of reagents, such as with $MnO_2$, $HNO_3$, DDQ, or other methods known in the art. A preferred method involves treating (5) with 70% aqueous nitric acid in acetic acid as solvent to afford pyridine (6). Reaction of chloromethylpyridine (6) with potassium cyanide or sodium cyanide, in a solvent such as ethanol or N,N-dimethylformamide, at elevated temperature, can produce the nitrile (7), in which an additional carbon atom has been introduced. Reduction of the nitrile (7) can be accomplished by a variety of procedures known to those skilled in the art. A preferred procedure is catalytic hydrogenation using a catalyst such as Pd/C, in a solvent such as methanol or ethanol, which gives a primary amine. This primary amine can then undergo intramolecular ring closure, which can be spontaneous or can be facilitated by heating in a suitable solvent, such as methanol or ethanol, to afford the lactam (8). If $R^b$ is benzyl, catalytic hydrogenation will afford a carboxylic acid (where $R^b$ is H). Transformation of ester or acid (8) to the primary alcohol (9) can be performed using any of the methods known in the art. For example, when $R^b$=Me, the ester (8) can be reduced with a suitable hydride reducing agent such as $LiBH_4$. When $R^b$=H, the acid (8) can be converted to an activated ester such as a mixed anhydride, using a base such as triethylamine and then ethyl chloroformate, and then reduced with a reagent such as $NaBH_4$. Alternatively, the acid (8) can be converted to the acid chloride with oxalyl chloride or thionyl chloride and then reduced with a suitable reducing agent, such as $NaBH_4$, $LiAlH_4$ or lithium tri-tert-butoxy aluminum hydride. The resulting alcohol (9) can then be converted to a mesylate or chloride using reagents such as $CH_3SO_2Cl$, in solvents such methylene chloride or tetrahydrofuran, and in the presence of a base such as triethylamine. The desired primary amines (10) can then be obtained by reaction of the precursor chloride or mesylate with $NH_3$/MeOH under thermal or microwave heating conditions.

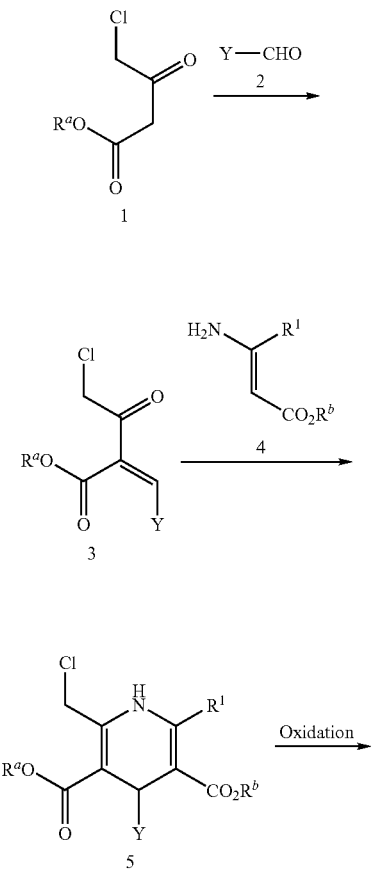

SCHEME 1

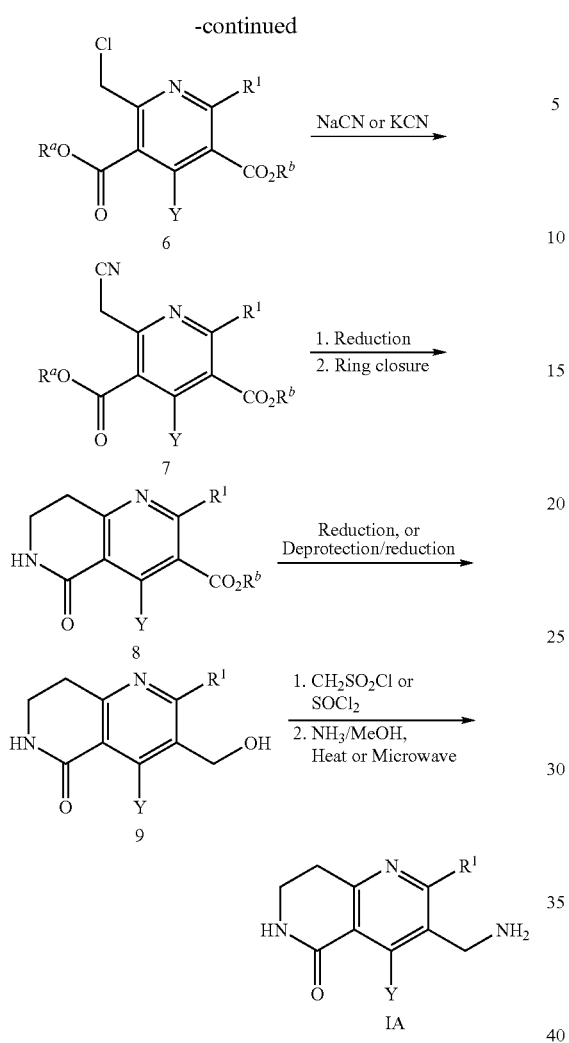

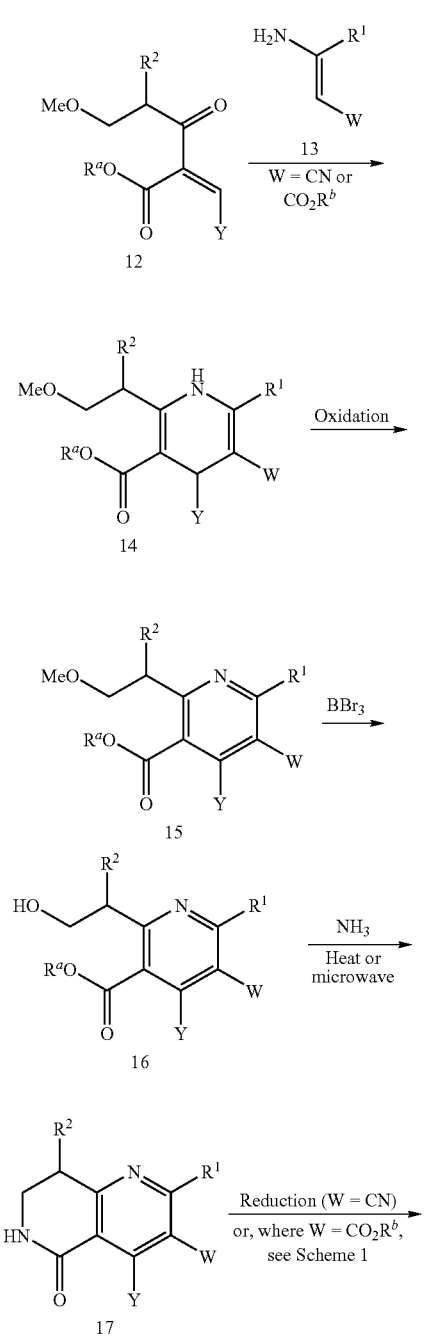

prepare the desired aminomethyl 7,8-dihydro-1,6-naphthyridin-5(6H)-ones of formula IA'.

Scheme 2 provides an alternative route to prepare aminomethyl 7,8-dihydro-1,6-naphthyridin-5(6H)-ones of formula (IA'). A ketoester of formula (II), obtained from commercial sources or prepared by procedures known to those skilled in the art, can be condensed with aldehyde (2) under mild acidic catalysis, as described in Scheme 1, to form the conjugated ester (12). Also following Scheme 1, reaction of enamine (13) with ester (12) affords the dihydropyridine of formula (14). Enamines of formula (13) can be obtained from commercial sources or can be prepared by reaction of the corresponding ketoester or ketonitrile with ammonia. Oxidation of dihydropyridine (14) to pyridine (15) can be performed with $MnO_2$, $HNO_3$, or other methods known in the art. A preferred method involves treating (14) with 70% aqueous nitric acid in acetic acid as solvent to afford pyridine (15). Demethylation of the methyl ether can be accomplished with $BBr_3$ under standard literature conditions to afford the alcohol (16). Heating alcohol (16) directly with an ammonia source, such as with ammonium hydroxide, in a sealed tube at elevated temperature or under microwave conditions, can afford the 7,8-dihydro-1,6-naphthyridin-5(6H)-ones (17). When W is CN, direct reduction, such as by hydrogenation using Raney nickel as a catalyst, affords the desired aminomethyl 7,8-dihydro-1,6-naphthyridin-5(6H)-ones of formula (IA'). When W is $CO_2R_b$, the procedures described in Scheme 1 can be used to -continued

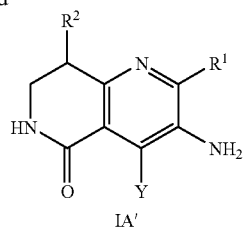

The alcohol (16) can be used in a variety of ways to prepare additional compounds of this invention, as shown in Scheme 3. Under certain conditions, such as acidic conditions, for example by direct concentration of the reaction mixture of the $BBr_3$-mediated methoxy demethylation in Scheme 2, the alcohol (16) can close onto the ester to form the lactone (19). The alcohol (16) can also be activated by converting it into a leaving group, such as the mesylate (20). Under certain conditions, such as by exposure to basic conditions, an elimination can occur to afford the olefins (21). Each of these materials, compounds (19), (20), and (21) can be used to prepare additional compounds of this invention.

SCHEME 3

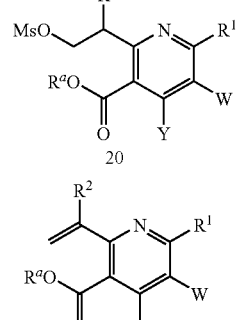

As shown in Scheme 4, the lactone (19), mesylate (20) and olefin (21) can each be treated with an appropriate primary amine $A-NH_2$, for example glycine derivatives or alkylamines, typically under heating or microwave conditions and also typically in the presence of a suitable base, such as triethylamine, to afford 7,8-dihydro-1,6-naphthyridin-5(6H)-ones (22). These compounds (22) can be converted into the desired aminomethyl 7,8-dihydro-1,6-naphthyridin-5(6H)-ones IB of the invention by procedures that have been described in Schemes 1 and 2.

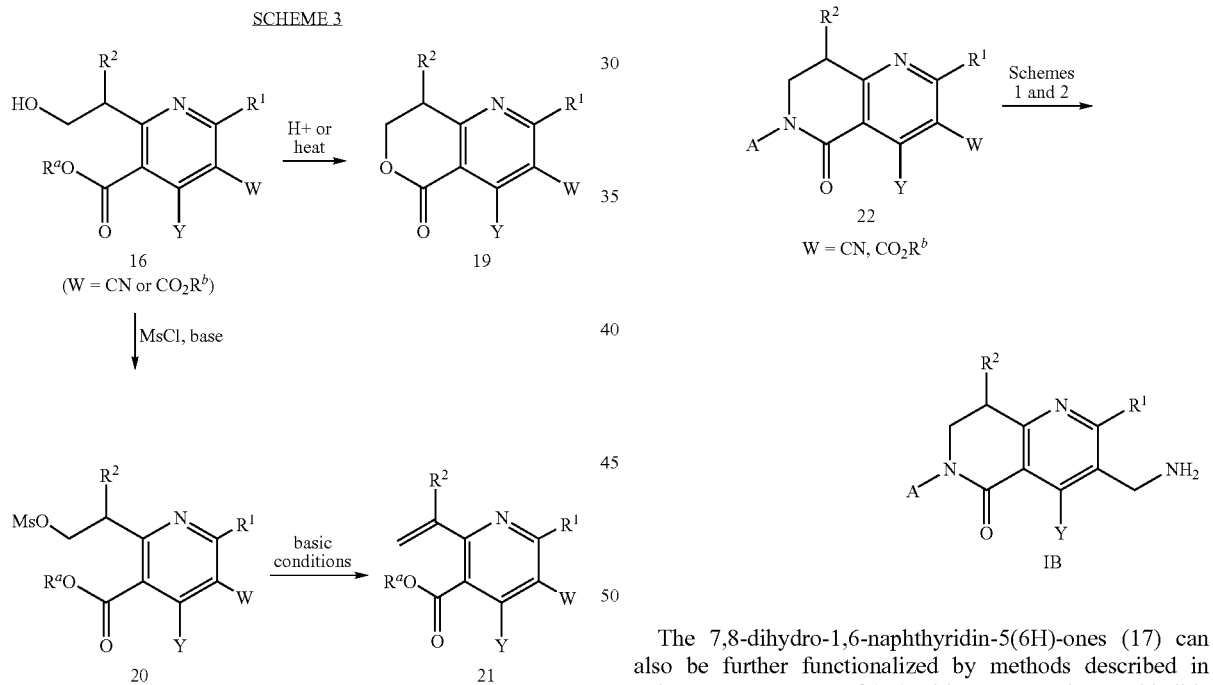

The 7,8-dihydro-1,6-naphthyridin-5(6H)-ones (17) can also be further functionalized by methods described in Scheme 5. Treatment of (17) with an appropriate aryl halide in the presence of CuI, a diamine ligand, such as N,N'-dimethylethylenediamine, and a base, such as $K_2CO_3$ or $Cs_2CO_3$, at elevated temperature can afford compounds (24), where A=aryl (see, for example, J. Am. Chem. Soc., 124:7421 (2002)). Conversion of W to the aminomethyl 7,8-dihydro-1,6-naphthyridin-5(6H)-ones (IB') follows procedures described in earlier Schemes. Additionally, deprotonation of (17) with a suitable base, such as sodium hydride, followed by treatment with suitable electrophiles, such as alkyl halides, aryl and alkyl sulfonyl chlorides, alkoxycarbonylmethyl halides, etc., can afford substituted lactams (26), which can be elaborated to the aminomethyl 7,8-dihydro-1,6-naphthyridin-5(6H)-ones (IB") as described in earlier Schemes.

SCHEME 5

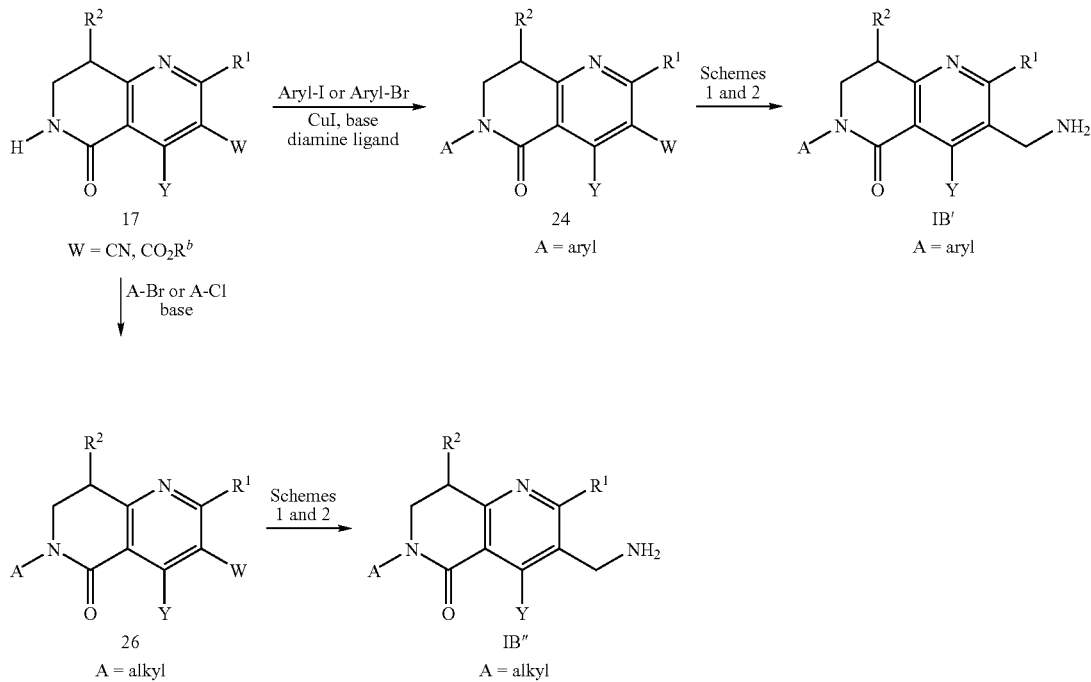

Scheme 6 describes an additional strategy for functionalizing the lactam. Compound (IA'), readily available as described in earlier schemes, can be protected by a wide variety of N-protecting groups which are well known to those skilled in the art, such as BOC, bis-BOC, CBZ, etc., to afford N-protected compounds (29). Lactam functionalization as described in Scheme 5 can afford compounds (30), which upon N-deprotection will then afford the desired aminomethyl 7,8-dihydro-1,6-naphthyridin-5(6H)-ones (IB).

SCHEME 6

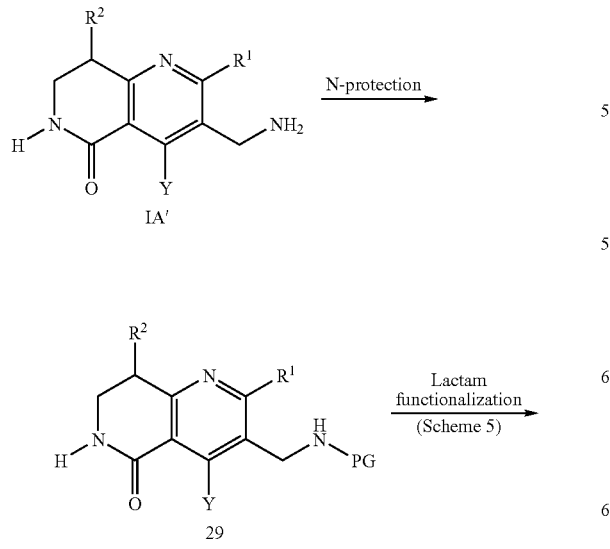

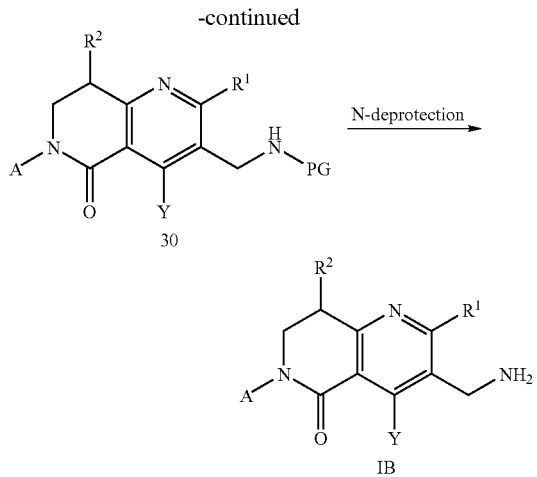

Scheme 7 provides a route to prepare aminomethyl 1,6-naphthyridine-5,7(6H,8H)-diones (IC) of the present invention, where X and Z are C=O, n is 1 and b is a single bond. A ketoester of formula (32) (where $R^c$ is alkyl), obtained from commercial sources or prepared by procedures known to those skilled in the art, can be reacted with aldehyde (2) as described previously to form the conjugated ester (33), which after reacting with enamine (13) can yield a dihydropyridine of formula (34).

Enamines of formula (13) can be obtained from commercial sources or can be prepared by reaction of the corresponding ketoester or ketonitrile with ammonia.

Oxidation of dihydropyridine (34) to pyridine (35) can be performed with $MnO_2$, $HNO_3$, or other methods known in the art, as described previously. Heating (35) directly with an appropriate amine $A-NH_2$, such as with ammonium hydroxide or an alkylamine or arylamine, in a sealed tube at elevated temperature or under microwave conditions, can afford the 1,6-naphthyridine-5,7(6H,8H)-diones (36). The desired aminomethyl 1,6-naphthyridine-5,7(6H,8H)-diones (IC) of the present invention can be obtained following the procedures described in Schemes 1 and 2.

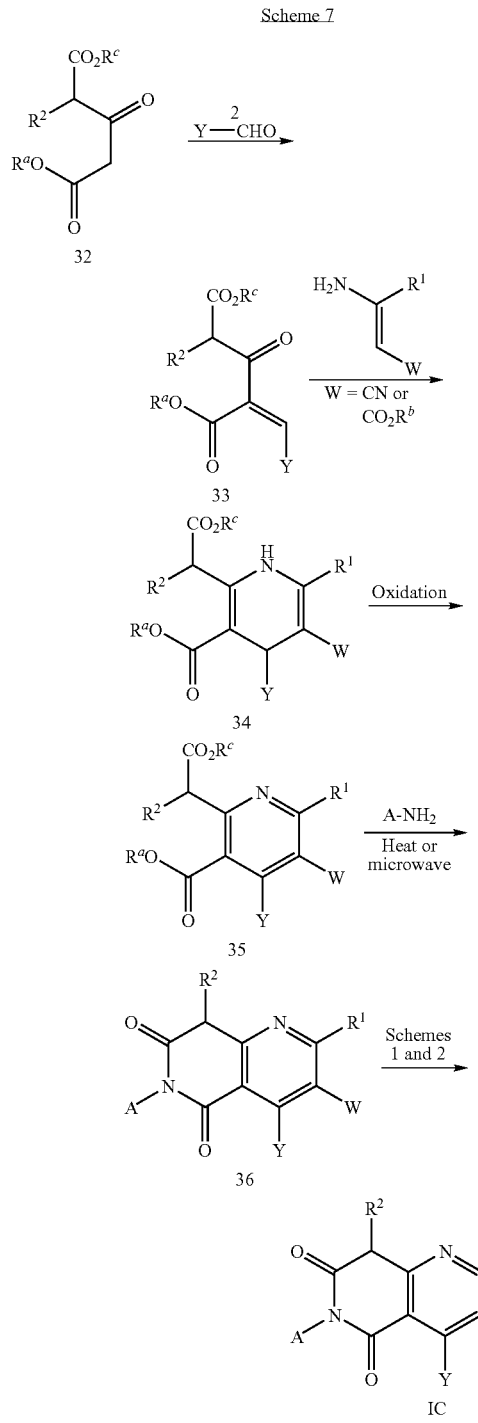

monocarboxylic acid (38) can be readily accomplished when $R_a$ and $R^c$ are different, as will be appreciated by one skilled in the art. For example, if $R_a$ is methyl and $R^c$ is tert-butyl, saponification with a base such as lithium hydroxide will provide (38). Conversely, if $R^a$ is tert-butyl and $R^c$ is methyl, treatment of (35) with an acid such as trifluoroacetic acid will provide (38). Using standard procedures known to those skilled in the art, the acid functionality of (38) can be readily reduced to an alcohol, such as by treatment with borane in a solvent such as THF, or by formation of a mixed anhydride with ethyl chloroformate and a base such as triethylamine, followed by reduction of the mixed anhydride with a reducing agent such as sodium borohydride. The resulting alcohol can be oxidized to the aldehyde (39) by a variety of procedures, such as by treatment with $MnO_2$ or by Swern oxidation. Treatment of (39) with an appropriate amine $A-NH_2$ under reductive amination conditions, such as by using a reducing agent such as sodium triacetoxyborohydride or sodium cyanoborohydride under mildly acidic conditions in solvent such as methanol or methylene chloride, will afford a benzylamine. This benzylamine can add in an intramolecular fashion to the ester functionality $CO_2R^c$ to form the lactam (40), the ring-closure either occurring spontaneously, or under conditions such as heating in an appropriate solvent. The desired aminomethyl 5,6-dihydro-1,6-naphthyridin-7(8H)-ones (ID) of the present invention can be obtained following the procedures described in Schemes 1 and 2.

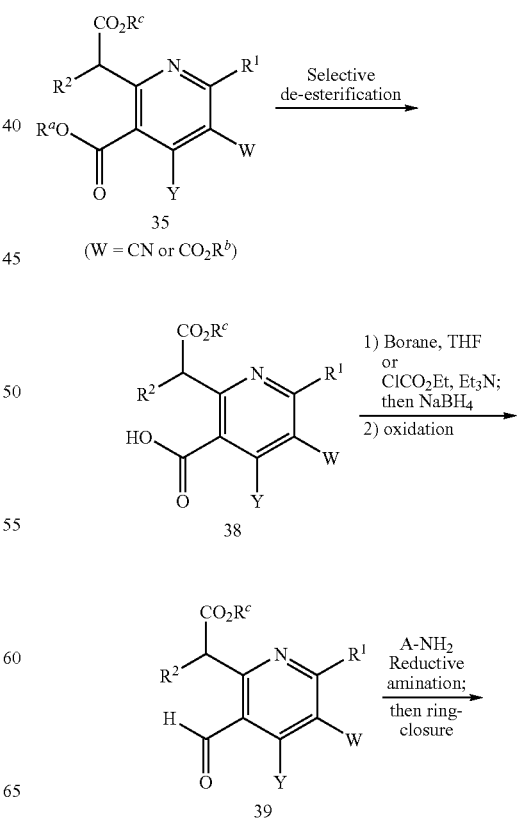

Scheme 8 provides a route to 5,6-dihydro-1,6-naphthyridin-7(8H)-ones (ID), where Z is $CH_2$, X is C=O, and n is 1. Selective de-esterification of the diester (35) to give the

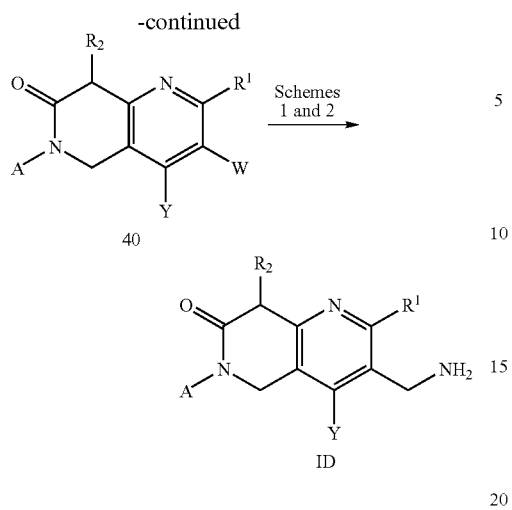

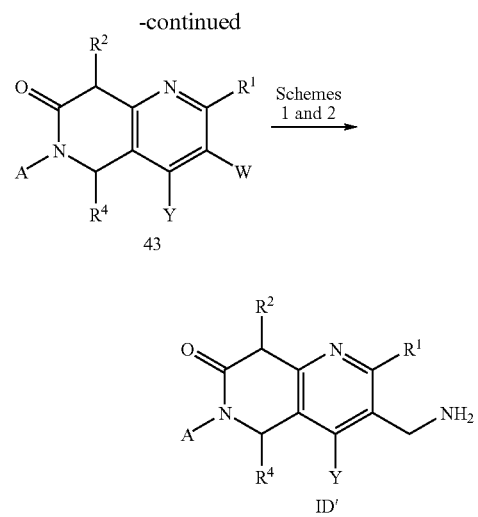

Scheme 9 provides a route to 5,6-dihydro-1,6-naphthyridin-7(8H)-ones ID', where Z is CHR$^4$, X is C=O, and n is 1. The aldehyde (39) from Scheme 8 can be treated with a variety of organometallic agents R$^4$-M, such as alkyl or aryl Grignard reagents and the like, usually at low temperatures such as −78° C. to 0° C. and in solvents such as THF and ether, to afford secondary alcohols. These secondary alcohols can be oxidized to the ketone (42) by a variety of procedures known to those skilled in the art, such as by treatment with MnO$_2$ or by Swern oxidation. As described in Scheme 8, treatment of (42) with an appropriate amine A-NH$_2$ under reductive amination conditions, such as by using a reducing agent such as sodium triacetoxyborohydride or sodium cyanoborohydride under mildly acidic conditions in solvents such as methanol or methylene chloride, will afford a benzylamine. This benzylamine can add in an intramolecular fashion to the ester functionality CO$_2$R$^c$ to form the lactam (43), the ring-closure either occurring spontaneously, or under conditions such as heating in an appropriate solvent. The desired aminomethyl 5,6-dihydro-1,6-naphthyridin-7(8H)-ones (ID') of the present invention, where X is C=O, Z is CHR$^4$ and n is 1, can be obtained following the procedures described in Schemes 1 and 2.

SCHEME 9

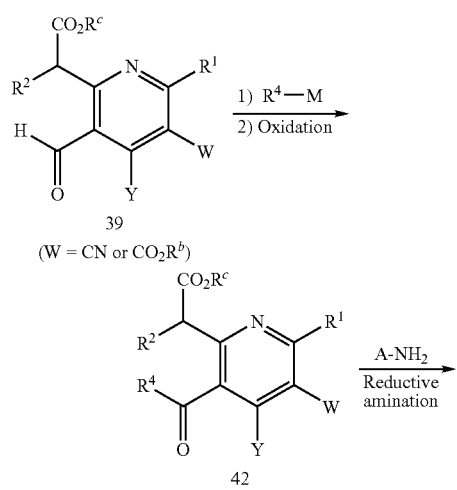

Scheme 10 provides a route to 5,6-dihydro-1,6-naphthyridin-7(8H)-ones IE, where Z is C=O, X is CR$^3$, and n is 1. Selective de-esterification of the diester (35) to give the monocarboxylic acid (45) can be readily accomplished when R$^a$ and R$^c$ are different, as will be appreciated by one skilled in the art (see Greene, T. and Wuts, P. G. M., Protecting Groups in Organic Synthesis, John Wiley & Sons, Inc., New York, N.Y. (1991) and references therein). For example, if R$^c$ is methyl and R$^a$ is tert-butyl, saponification with a base such as lithium hydroxide will provide (45). Conversely, if R$^c$ is tert-butyl and R$^a$ is methyl, treatment of (35) with an acid such as trifluoroacetic acid will provide (45). Using standard procedures known to those skilled in the art, the acid functionality of (45) can be readily reduced to an alcohol, such as by treatment with borane in a solvent such as THF, or by formation of a mixed anhydride with ethyl chloroformate and a base such as triethylamine, followed by reduction of the mixed anhydride with a reducing agent such as sodium borohydride. The resulting alcohol can be oxidized to the aldehyde (46) by a variety of procedures, as described previously, such as by treatment with MnO$_2$ or by Swern oxidation. Treatment of (46) with a variety of organometallic agents R$^3$-M, such as alkyl or aryl Grignard reagents and the like, usually at low temperatures such as −78° C. to 0° C. and in solvents such as THF and ether, affords secondary alcohols. These secondary alcohols can be oxidized to the ketone (47) by a variety of procedures known to those skilled in the art, such as by treatment with MnO$_2$ or by Swern oxidation. Treatment of (47) with an appropriate amine A-NH$_2$ under reductive amination conditions, as described previously, such as by using a reducing agent such as sodium triacetoxyborohydride or sodium cyanoborohydride under mildly acidic conditions in solvent such as methanol or methylene chloride, will afford a benzylamine. This benzylamine can add in an intramolecular fashion to the ester functionality CO$_2$R$^a$ to form the lactam (48), the ring-closure either occurring spontaneously, or under conditions such as heating in an appropriate solvent. The desired aminomethyl 5,6-dihydro-1,6-naphthyridin-7 (8H)-ones (1E) of the present invention, where Z is C=O, X is CHR$^3$ and n is 1, can be obtained following the procedures described in Schemes 1 and 2.

SCHEME 10

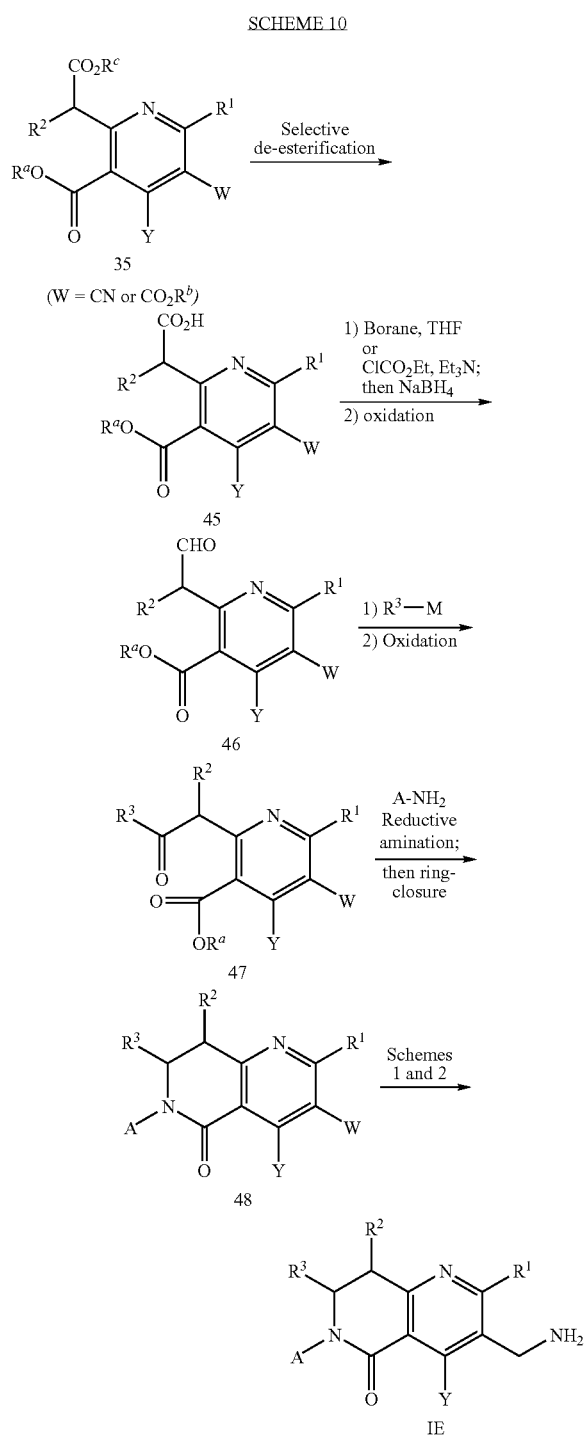

ods are well known to those skilled in the art (see Greene, T. and Wuts, P. G. M., *Protecting Groups in Organic Synthesis*, John Wiley & Sons, Inc., New York, N.Y. (1991) and references therein). Using standard procedures known to those skilled in the art, the acid functionality can be readily reduced to the alcohol (51), such as by treatment with borane in a solvent such as THF, or by formation of a mixed anhydride with ethyl chloroformate and a base such as triethylamine, followed by reduction of the mixed anhydride with a reducing agent such as sodium borohydride. The alcohol (51) can then be converted to a mesylate or chloride using reagents such as $CH_3SO_2Cl$ or $SOCl_2$ in solvents such methylene chloride or tetrahydrofuran, and with or without a base such as triethylamine. Treatment of the chloride or mesylate with sodium cyanide or potassium cyanide, in solvents such as acetonitrile or DMF, affords the nitrile (52). The nitrile (52) can be reduced by a variety of procedures, such as by catalytic hydrogenation using catalysts such as Raney nickel or Pd/C, or by treating the nitrile with a reducing agent such as sodium borohydride in the presence of a catalyst such as $NiCl_2$ or $CoCl_2$, to afford compounds of the present invention (IF), where n is 2.

SCHEME 11

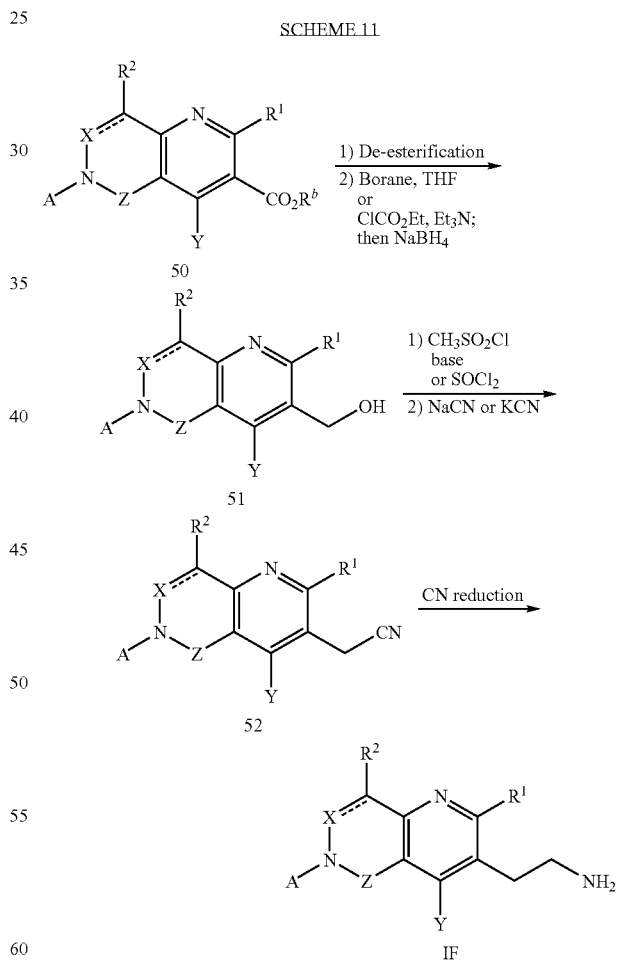

Scheme 11 provides a route to compounds of the present invention where n is 2. Ester (50) represents intermediates useful for preparation of compounds of the present invention as described in Schemes 1 to 10. For example, where Z is C=O, A is H, X is $CH_2$, $R^2$ is H, and the bond b is single, compound (50) represents compound (8) which can be prepared as described in Scheme 1. De-esterification of ester (50) can be readily accomplished in a variety of ways depending on the nature of $R_b$ to provide a carboxylic acid. These meth- Scheme 12 provides a route to additional compounds of the present invention. Treatment of (54), where X is $CHR^3$ and Z is C=O, with Lawesson's reagent provides the thioamide compound (55), which can be used to prepare compounds of the present invention (as described in Schemes 1 and 2) where Z is C=S. Reduction of the amide functionality of (54), such as by treating with borane in a solvent such as THF, provides (56), which can be used to prepare compounds of the present invention (as described in Schemes 1 and 2) where Z is CH$_2$. In the same manner, treatment of (57), where Z is CHR$^4$ and X is C=O, with Lawesson's reagent provides the thioamide compound (58), which can be used to prepare compounds of the present invention (as described in Schemes 1 and 2) where X is C=S. Reduction of the amide functionality of (57), such as by treating with borane in a solvent such as THF, provides (59), which can be used to prepare compounds of the present invention (as described in Schemes 1 and 2) where X is CH$_2$.

SCHEME 12

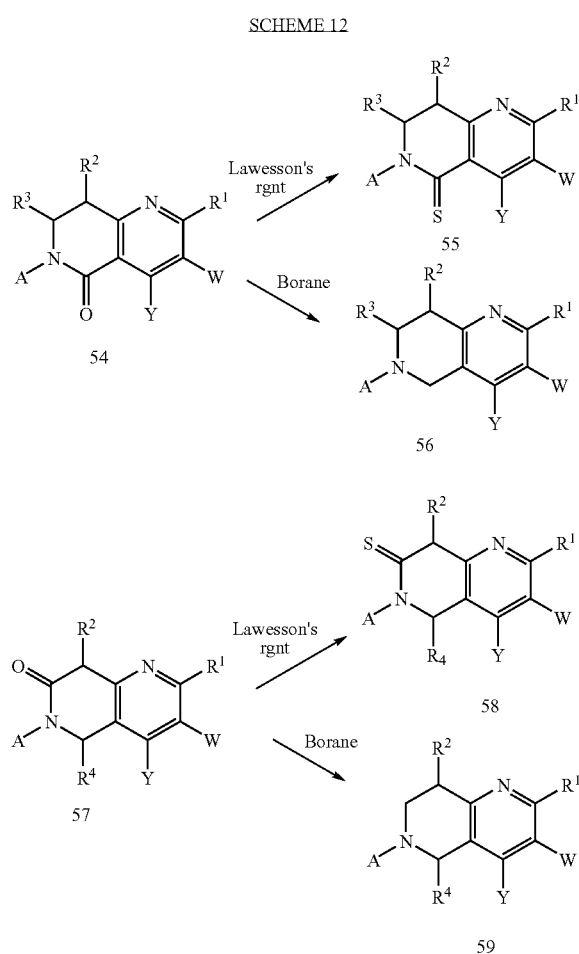

SCHEME 13

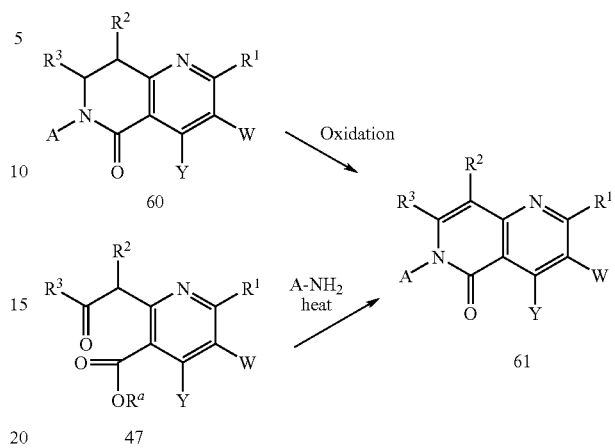

Scheme 13 provides a route to compounds of the present invention where bond b is double. Compound (60) (which can be converted to a compound of the invention where Z is C=O and bond b is single (employing Schemes 1 and 2)), can be oxidized to compound (61), where bond b is double, by various oxidizing agents such as DDQ and MnO$_2$. Alternatively, compound (47) from Scheme 10 can be treated with an appropriate amine A-NH$_2$, which can form an imine/enamine intermediate, which upon heating can condense onto the ester functionality CO$_2$R$^a$ to provide compound (61), where bond b is double. Compound (61) can be used to prepare compounds of the invention employing the procedures of Schemes 1 and 2.

All product amines that exist as atropisomers can be separated into individual enantiomers using methods known in the art. For example, resolution by crystallization of diastereomeric salts (tartaric acid, N-protected amino acids, etc; see for example, Eliel, Ernest L.; Wilen, Samuel H.; Doyle, Michael P., *Basic Organic Stereochemistry*, Wiley, (2001)), chiral preparative HPLC, use of enzymes, use of chiral derivatizing agents (see for example, *J. Org. Chem.*, 48(15):2520-2527 (1983)), or preparation and chromatographic separation of diastereomeric derivatives. Alternatively, these methods can be applied to any of the intermediates in the synthesis of these product amines.

DEFINITIONS

The following definitions apply to the terms as used throughout this specification, unless otherwise limited in specific instances.

Unless otherwise indicated, the term "alkyl" or "alk" as used herein alone or as part of another group includes both branched and straight-chain saturated aliphatic hydrocarbon radicals/groups having the specified number of carbon atoms. In particular, "Alkyl" refers to a monoradical branched or unbranched saturated hydrocarbon chain, preferably having from 1 to 40 carbon atoms, more preferably 1 to 10 carbon atoms, even more preferably 1 to 6 carbon atoms, such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like, unless otherwise indicated. Unless otherwise constrained by the definition for the alkyl substituent, such alkyl groups can optionally be substituted with one, two or three or more substituents selected from a member of the group consisting of halo, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl", "carbocycle" or "carbocyclic" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl, which includes, for example cyclopropyl, cyclobutyl, cyclopentyl, cyclohexyl, cycloheptyl, cyclooctyl, cyclodecyl and cyclododecyl, cyclohexenyl,

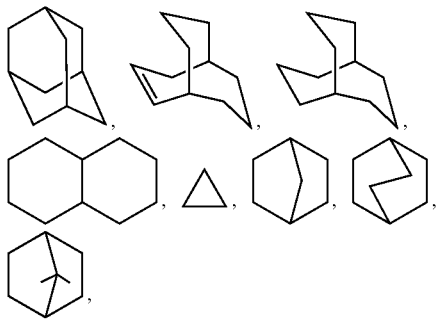

any of which groups may be optionally substituted with 1 to 3 or more substituents such as of the substituents for described herein for alkyl or aryl.

The term "Aryl" or "Ar" as used herein alone or as part of another group refers to an unsaturated aromatic carbocyclic group of from 5 to 20 carbon atoms having a single ring (e.g., phenyl) or multiple condensed (fused) rings (e.g., naphthyl or anthryl). Representative examples include, but are not limited to, aromatic radicals such as phenyl, naphthyl, tetrahydronaphthyl, indane and biphenyl. Unless otherwise constrained by the definition for the aryl substituent, such aryl groups can optionally be substituted with one to three or more substituents selected from a member of the group consisting of hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, any of the alkyl substituents described herein, or substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "cycloheteroalkyl", "heterocyclo", "heterocyclic group" or "heterocyclyl" as used herein alone or as part of another group refers to a saturated or unsaturated group having a single ring, multiple condensed rings or multiple covalently joined rings, from 1 to 40 carbon atoms and from 1 to 10 hetero ring atoms, preferably 1 to 4 hetero ring atoms, selected from nitrogen, sulfur, phosphorus, and/or oxygen. Preferably, "Heterocycle" or "Heterocyclic group" means a stable 5 to 7 membered monocyclic or bicyclic or 7 to 10 membered bicyclic heterocyclic ring that may be saturated, partially unsaturated, or aromatic, and that comprises carbon atoms and from 1 to 4 heteroatoms independently selected from a member of the group consisting of nitrogen, oxygen and sulfur and wherein the nitrogen and sulfur heteroatoms are optionally be oxidized and the nitrogen heteroatom may optionally be quaternized, and including any bicyclic group in which any of the above-defined heterocyclic rings is fused to a benzene ring. The heterocyclic groups may be substituted on carbon or on a nitrogen, sulfur, phosphorus, and/or oxygen heteroatom, such as, but not limited to, 1 to 3 or more substituents described for alkyl or aryl herein, so long as the resulting compound is stable. For example:

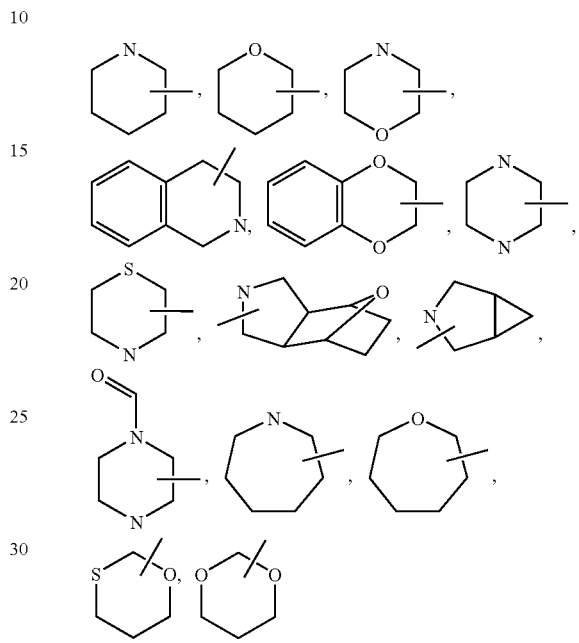

and the like.

"Heteroaryl" as used herein alone or as part of another group embraces unsaturated heterocyclic radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g., 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g., benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like. Further, examples of heteroaryl groups include the following:

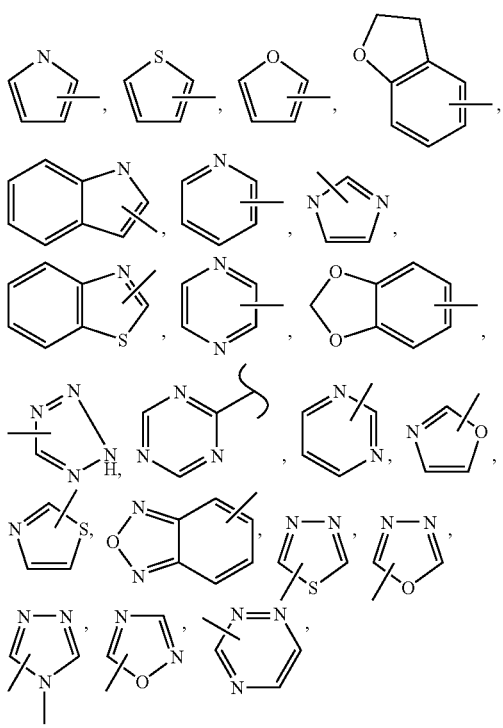

and the like. Unless otherwise constrained by the definition for the heteroaryl substituent, such heteroaryl groups can optionally be substituted with one to three or more substituents, such as those described for alkyl or aryl herein.

Unless otherwise indicated, the term "alkenyl" as used herein alone or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Optionally, said alkenyl group may be substituted with one to three or more substituents, such as those substituents disclosed for alkyl.

Unless otherwise indicated, the term "alkynyl" as used herein alone or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. Optionally, said alkynyl group may be substituted with one to three or more substituents, such as those substituents disclosed for alkyl.

The term "cycloalkenyl" as employed herein alone or as part of another group refers to partially unsaturated cyclic hydrocarbons containing 3 to 12 carbons, preferably 5 to 10 carbons and 1 or 2 double bonds. Exemplary cycloalkenyl groups include cyclobutenyl, cyclopentenyl, cyclohexenyl, cycloheptenyl, cyclooctenyl, cyclohexadienyl, and cycloheptadienyl. Optionally, said cycloalkenyl group may be substituted with one to three or more substituents, such as those substituents disclosed for alkyl.

The term "bicycloalkyl" as employed herein alone or as part of another group includes saturated bicyclic ring groups such as, without limitation, [3.3.0]bicyclooctane, [4.3.0]bicyclononane, [4.4.0]bicyclodecane (decalin), [2.2.2]bicyclooctane, and so forth.

The term "polycycloalkyl" as employed herein alone or as part of another group includes two or more cycloalkyl ring systems, as defined herein, wherein at least one carbon atom is a part of at least two separately identifiable ring systems. The polycycloalkyl group may contain bridging between two carbon atoms, for example, bicyclo[1.1.0]butyl, bicyclo[3.2.1]octyl, bicyclo[5.2.0]nonyl, tricycl[2.2.1.0.sup.1]heptyl, norbornyl and pinanyl. The polycycloalkyl group may contain one or more fused ring systems, for example, decalinyl (radical from decalin) and perhydroanthracenyl. The polycycloalkyl group may contain a spiro union, in which a single atom is the only common member of two rings, for example, spiro[3.4]octyl, spiro[3.3]heptyl and spiro[4.5]decyl.

The term "halogen" or "halo" as used herein alone or as part of another group refers to chlorine, bromine, fluorine, and iodine as well as $CF_3$.

The term "alkoxy" or "alkyloxy" as used herein alone or as part of another group, refers to an alkyl group, as defined herein, appended to a parent molecular moiety through an alkyl group, as defined herein.

The term "haloalkoxy" as used herein alone or as part of another group refers to alkoxy radicals, as defined herein, further substituted with one or more halo atoms, such as fluoro, chloro or bromo, to provide haloalkoxy radicals. Examples include, without limitation, fluoromethoxy, chloromethoxy, trifluoromethoxy, trifluoromethoxy, fluoroethoxy and fluoropropoxy.

The term "acyl" as employed herein by itself or part of another group, as defined herein, refers to an organic radical linked to a carbonyl

group; examples of acyl groups include a substituent group attached to a carbonyl, such as alkanoyl, alkenoyl, aroyl, aralkanoyl, heteroaroyl, cycloalkanoyl, cycloheteroalkanoyl and the like.

The term "cycloalkylalkyl", "arylalkyl", "cycloheteroalkyl", "bicycloalkylalkyl" or "heteroarylalkyl" as used herein alone or as part of another group, refers to a cycloalkyl, an aryl, a cyclohetero, a bicycloalkyl or heteroaryl group, as defined herein, appended to a parent molecular moiety through an alkyl group, as defined herein. Representative examples of arylalkyl include, but are not limited to, benzyl, 2-phenylethyl, 3-phenylpropyl, and the like.

The term "cycloheteroalkylalkyl" as used herein alone or as part of another group refers to a cycloheteroalkyl group as defined herein, linked through a C atom or heteroatom to a $(CH_2)_r$ chain, where "r" can be 1 to 10.

The term "polyhaloalkyl" as used herein alone or as part of another group refers to an "alkyl" group as defined above, having 2 to 9, preferably from 2 to 5, halo substituents, such as $CF_3CH_2$, $CF_3$ or $CF_3CF_2CH_2$.

The term "polyhaloalkoxy" as used herein refers to an "alkoxy" or "alkyloxy" group as defined above having 2 to 9, preferably from 2 to 5, halo substituents, such as $CF_3CH_2O—$, $CF_3O—$ or $CF_3CF_2CH_2O—$.

The term "thiol" or "thio" as used herein alone or as part of another group, refers to (—S) or (—S—).

The term "alkylthio" or "arylalkylthio" refers to an alkyl group or and arylalkyl group, as defined herein, linked to a parent molecular moiety through a thiol group.

The term "alkylthioalkyl" or "arylalkylthioalkyl" refers to an alkylthio group or and arylalkylthio group, as defined herein, linked to a parent molecular moiety through an alkyl group.

The term "hydroxy" as used herein alone or as part of another group, refers to a —OH group.

The term "hydroxyalkyl" as used herein alone or as part of another group, refers to a hydroxyl group, as defined herein, appended to a parent molecular moiety through a alkyl group, as defined herein.

The term "cyano" as used herein alone or as part of another group, refers to a —CN group.

The term "nitro" as used herein, refers to a —$NO_2$ group.

The term "sulfinyl", whether used alone or linked to other terms such as alkylsulfinyl, denotes respectively divalent radicals —S(O)—.

The term "alkylsulfinyl" as used herein alone or as part of another group, refers to an alkyl group, as defined herein, appended to a parent molecular moiety through a sulfinyl group, as defined herein.

The term "sulfonyl" as used herein alone or as part of another group, refers to an $SO_2$ group.

The term "alkylsulfonyl" or "aminosulfonyl", as used herein, refer to an alkyl or amino group, as defined herein, appended to a parent molecular moiety through a sulfonyl group, as defined herein.

The term "amino" as employed herein, refers to an —$NH_3$ group or an amine linkage: —$NR_a$—, wherein Ra may be as described below in the definition for "substituted amino".

The term "substituted amino" as employed herein alone or as part of another group refers to amino substituted with one or two substituents. For example, $NR_aR_b$, wherein $R_a$ and $R_b$ may be the same or different and are, for example chosen from hydrogen, alkyl, cycloalkyl, alkenyl, cycloalkenyl, alkynyl, aryl, heteroaryl, heterocyclic, arylalkyl, heteroarylalkyl, cycloheteroalkyl, cycloheteroalkylalkyl, cycloalkylalkyl, haloalkyl, hydrooxyalkyl, alkoxyalkyl or thioalkyl. These substituents may optionally be further substituted with any of the alkyl substituents as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1piperazinyl, 4-arylalkyl-1piperazinyl, 4-diarylalkyl-1-piperazinyl, 1-pyrrolindinyl, 1-piperidinyl, or 1-azepinyl, optionally substituted with alkyl, alkoxy, alkylthio, halo, trifluoromethyl or hydroxyl.

The term "dialkylamino" as employed herein alone, or as part of another group, refers to a substituted amino group having two alkyl substituents. For example, $NR_aR_b$, wherein $R_a$ and $R_b$ are each an alkyl group, as defined herein.

The term "carbonyl" as used herein, refers to a —C(O)— group.

The term "aminocarbonyl", "alkylcarbonyl", "alkoxycarbonyl", "arylcarbonyl", "alkynylaminocarbonyl", "alkylaminocarbonyl" and "alkenylaminocarbonyl" as used herein, refer to an amino group, alkyl group, alkoxy group, aryl group, alkynylamino group, alkylamino group or an alkenylamino group, as defined herein, appended to a parent molecular moiety through a carbonyl group, as defined herein.

The term "heteroarylamino", "arylamino", "alkylamino", "alkylcarbonylamino", "arylcarbonylamino", "alkylsulfonylamino", "alkylaminocarbonylamino" or "alkoxycarbonylamino" as used herein, refers to a heteroaryl, aryl, alkyl, alkylcarbonyl, arylcarbonyl, alkylsulfonyl, alkylaminocarbonyl or alkoxycarbonyl group as defined herein, appended to a parent molecular moiety through an amino group, as defined herein.

The term "sulfonamido" refers to —$S(O)_2$—$NR_aR_b$, wherein $R_a$ and $R_b$ are as defined above for "substituted amino".

The term "alkylcarbonyloxy" as used herein, refers to an "alkyl-CO—O—" group, wherein alkyl is as defined above.

"Optional" or "optionally" means that the subsequently described event or circumstance may or may not occur, and that the description includes, without limitation, instances where said event or circumstance occurs and instances in which it does not. For example, optionally substituted alkyl means that alkyl may or may not be substituted by those groups enumerated in the definition of substituted alkyl.

"Substituted," as used herein, whether express or implied and whether preceded by "optionally" or not, means that any one or more hydrogen on the designated atom (C, N, etc.) is replaced with a selection from the indicated group, provided that the designated atom's normal valency is not exceeded, and that the substitution results in a stable compound. For instance, when a $CH_2$ is substituted by a keto substituent (=O), then 2 hydrogens on the atom are replaced. Combinations of substituents and/or variables are permissible only if such combinations result in stable compounds. Further, when more than one position in a given structure may be substituted with a substituent selected from a specified group, the substituents may be either the same or different at every position.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Various forms of prodrugs are well known in the art. A comprehensive description of prodrugs and prodrug derivatives are described in:

a) *The Practice of Medicinal Chemistry*, Camille G. Wermuth et al., Ch. 31 (Academic Press, 1996);

b) *Design of Prodrugs*, edited by H. Bundgaard (Elsevier, 1985); and c) *A Textbook of Drug Design and Development*, P. Krogsgaard-Larson and H. Bundgaard, eds. Ch. 5, pp. 113-191 (Harwood Academic Publishers, 1991). Said references are incorporated herein by reference.

The conditions, diseases and maladies collectively referred to as "diabetic complications" include retinopathy, neuropathy and nephropathy, erectile dysfunction, delayed wound healing, and other known complications of diabetes.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The term "other type of therapeutic agents" as employed herein includes, but is not limited to one or more antidiabetic agents (other than DPP-IV inhibitors of formula I), one or more anti-obesity agents, one or more anti-hypertensive agents, one or more anti-platelet agents, one or more anti-atherosclerotic agents and/or one or more lipid-lowering agents (including anti-atherosclerosis agents).

Utilities and Combinations

Utilities

The compounds of the present invention possess activity as inhibitors of the dipeptidyl peptidase IV which is found in a variety of tissues, such as the intestine, liver, lung and kidney of mammals. Via the inhibition of dipeptidyl peptidase IV in vivo, the compounds of the present invention possess the ability to potentiate endogenous levels of GLP-1(7-36) and attenuate formation of its antagonist GLP-1(9-36).

Accordingly, the compounds of the present invention can be administered to mammals, preferably humans, for the treatment of a variety of conditions and disorders, including, but not limited to, treating or delaying the progression or onset of diabetes (preferably Type II, impaired glucose tolerance, insulin resistance, and diabetic complications, such as nephropathy, retinopathy, neuropathy and cataracts), hyperglycemia, hyperinsulinemia, hypercholesterolemia, elevated blood levels of free fatty acids or glycerol, hyperlipidemia, hypertriglyceridemia, obesity, wound healing, tissue ischemia, atherosclerosis and hypertension. The compounds of the present invention may also be utilized to increase the blood levels of high density lipoprotein (HDL).

In addition, the conditions, diseases, and maladies collectively referenced to as "Syndrome X" or Metabolic Syndrome as detailed in Johannsson, *J. Clin. Endocrinol. Metab.*, 82:727-34 (1997), may be treated employing the compounds of the invention.

Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

Other "therapeutic agent(s)" suitable for combination with the compound of the present invention include, but are not limited to, known therapeutic agents useful in the treatment of the aforementioned disorders including: anti-diabetic agents; anti-hyperglycemic agents; hypolipidemic/lipid lowering agents; anti-obesity agents; anti-hypertensive agents, and appetite suppressants. Additional therapeutic agents suitable for combination with the compound of the present invention include agents for treating infertility, agents for treating polycystic ovary syndrome, agents for treating a growth disorder and/or frailty, an anti-arthritis agent, agents for preventing inhibiting allograft rejection in transplantation, agents for treating autoimmune disease, an anti-AIDS agent, agents for treating inflammatory bowel disease/syndrome, agents for treating anorexia nervosa and an anti-osteoporosis agent.

Examples of suitable anti-diabetic agents for use in combination with the compound of the present invention include biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, PPARdelta agonists, PPARalpha/gamma/delta triple agonists, glycogen phosphorylase inhibitors, inhibitors of fatty acid binding protein (aP2), glucagon-like peptide-1 (GLP-1) or other agonists of the GLP-1 receptor, SGLT2 inhibitors and other dipeptidyl peptidase IV (DPP4) inhibitors.

Other suitable thiazolidinediones include Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi).

Examples of PPAR-alpha agonists, PPAR-gamma agonists, PPARdelta agonists, and PPAR alpha/gamma dual agonists include muraglitazar, peliglitazar, AR-H039242 (Astra/Zeneca), GW-409544 (Glaxo-Wellcome), GW-501516 (Glaxo-Wellcome), LY-919818 (Lilly/Ligand), KRP297 (Kyorin Merck) as well as those disclosed by Murakami et al., "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", *Diabetes*, 47:1841-1847 (1998), WO 01/21602 and in U.S. Pat. No. 6,653,314, the disclosure of which is incorporated herein by reference, employing dosages as set out therein, which compounds designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Suitable other DPP4 inhibitors include saxagliptin, those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, TSL-225 (tryptophyl-1,2,3,4-tetrahydroisoquinoline-3-carboxylic acid (disclosed by Yamada et al., *Bioorg. & Med. Chem. Lett.*, 8:1537-1540 (1998)), 2-cyanopyrrolidides and 4-cyanopyrrolidides, as disclosed by Ashworth et al., *Bioorg. & Med. Chem. Lett.*, 6(22): 1163-1166 and 2745-2748 (1996), the compounds disclosed in U.S. application Ser. No. 10/899,641, WO 01/68603 and U.S. Pat. No. 6,395,767, employing dosages as set out in the above references.

Other suitable meglitinides include nateglinide (Novartis) or KAD1229 (PF/Kissei).

Examples of suitable anti-hyperglycemic agents for use in combination with the compound of the present invention include glucagon-like peptide-1 (GLP-1), such as GLP-1(1-36) amide, GLP-1(7-36) amide, GLP-1(7-37) (as disclosed in U.S. Pat. No. 5,614,492), as well as exenatide (Amylin/Lilly), LY-315902 (Lilly), MK-0431 (Merck), liraglutide (NovoNordisk), ZP-10 (Zealand Pharmaceuticals A/S), CJC-1131 (Conjuchem Inc), and the compounds disclosed in WO 03/033671.

Examples of suitable hypolipidemic/lipid lowering agents for use in combination with the compound of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na+/bile acid co-transporter inhibitors, up-regulators of LDL receptor activity, bile acid sequestrants, cholesterol ester transfer protein (e.g., CETP inhibitors, such as CP-529414 (Pfizer) and JTT-705 (Akros Pharma)), PPAR agonists (as described above) and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440.

The HMG CoA reductase inhibitors which may be employed in combination with one or more compound of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compound of the present invention.

The squalene synthetase inhibitors suitable for use herein include, but are not limited to, α-phosphono-sulfonates disclosed in U.S. Pat. No. 5,712,396, those disclosed by Biller et al., *J. Med. Chem.*, 31(10):1869-1871 (1988), including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design*, 2:1-40 (1996).

In addition, other squalene synthetase inhibitors suitable for use herein include the terpenoid pyrophosphates disclosed by P. Ortiz de Montellano et al, *J. Med. Chem.*, 20:243-249 (1977), the farnesyl diphosphate analog $\underline{A}$ and presqualene pyrophosphate (PSQ-PP) analogs as disclosed by Corey and Volante, *J. Am. Chem. Soc.*, 98:1291-1293 (1976), phosphinylphosphonates reported by McClard, R. W. et al., *J.A.C.S.*, 109:5544 (1987) and cyclopropanes reported by Capson, T. L., Ph.D. dissertation, June, 1987, Dept. Med. Chem. U of Utah, Abstract, Table of Contents, pp 16, 17, 40-43, 48-51, Summary.

The fibric acid derivatives which may be employed in combination the compound of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination the compound of formula I include those disclosed in *Drugs of the Future*, 24:9-15 (1999) (Avasimibe); Nicolosi et al., "The ACAT inhibitor, CI-1011 is effective in the prevention and regression of aortic fatty streak area in hamsters", *Atherosclerosis* (Shannon, Irel.), 137(1):77-85 (1998); Ghiselli, Giancarlo, "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.*, 16(1):16-30 (1998); Smith, C. et al., "RP 73163: a bioavailable alkylsulfinyl-diphenylimidazole ACAT inhibitor", *Bioorg. Med. Chem. Lett.*, 6(1):47-50 (1996); Krause et al., "ACAT inhibitors: physiologic mechanisms for hypolipidemic and anti-atherosclerotic activities in experimental animals", Inflammation: Mediators Pathways, CRC, Boca Raton, Fla., publ., Ruffolo, Robert R., Jr., Hollinger, Mannfred A., eds., pp. 173-198 (1995); Sliskovic et al., "ACAT inhibitors: potential anti-atherosclerotic agents", *Curr. Med. Chem.*, 1(3):204-225 (1994); Stout et al., "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl] ureas with enhanced hypocholesterolemic activity", *Chemtracts: Org. Chem.*, 8(6):359-362 (1995), or TS-962 (Taisho Pharmaceutical Co. Ltd).

The hypolipidemic agent may be an up-regulator of LD2 receptor activity, such as MD-700 (Taisho Pharmaceutical Co. Ltd) and LY295427 (Eli Lilly).

Examples of suitable cholesterol absorption inhibitor for use in combination with the compound of the invention include SCH48461 (Schering-Plough), as well as those disclosed in *Atherosclerosis*, 115:45-63 (1995) and *J. Med. Chem.*, 41:973 (1998).

Examples of suitable ileal Na⁺/bile acid co-transporter inhibitors for use in combination with the compound of the invention include compounds as disclosed in *Drugs of the Future,* 24:425-430 (1999).

The lipoxygenase inhibitors which may be employed in combination the compound of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", *Brit. J. Pharmacology,* 120:1199-1206 (1997), and Cornicelli et al., "15-Lipoxygenase and its Inhibition: A Novel Therapeutic Target for Vascular Disease", *Current Pharmaceutical Design,* 5:11-20 (1999).

Examples of suitable anti-hypertensive agents for use in combination with the compound of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compound of the present invention include a beta 3 adrenergic agonist, a lipase inhibitor, a serotonin (and dopamine) reuptake inhibitor, a thyroid receptor beta drug, 5HT2C agonists, (such as Arena APD-356); MCHR1 antagonists such as Synaptic SNAP-7941 and Takeda T-226926, melanocortin receptor (MC4R) agonists, melanin-concentrating hormone receptor (MCHR) antagonists (such as Synaptic SNAP-7941 and Takeda T-226926), galanin receptor modulators, orexin antagonists, CCK agonists, NPY1 or NPY5 antagonist, NPY2 and NPY4 modulators, corticotropin releasing factor agonists, histamine receptor-3 (H3) modulators, 11-beta-HSD-1 inhibitors, adinopectin receptor modulators, monoamine reuptake inhibitors or releasing agents, a ciliary neurotrophic factor (CNTF, such as AXOKINE® by Regeneron), BDNF (brain-derived neurotrophic factor), leptin and leptin receptor modulators, cannabinoid-1 receptor antagonists (such as SR-141716 (Sanofi) or SLV-319 (Solvay)), and/or an anorectic agent.

The beta 3 adrenergic agonists which may be optionally employed in combination with compound of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983 and 5,488,064.

Examples of lipase inhibitors which may be optionally employed in combination with compound of the present invention include orlistat or ATL-962 (Alizyme).

The serotonin (and dopoamine) reuptake inhibitor (or serotonin receptor agonists) which may be optionally employed in combination with a compound of the present invention may be BVT-933 (Biovitrum), sibutramine, topiramate (Johnson & Johnson) or axokine (Regeneron).

Examples of thyroid receptor beta compounds which may be optionally employed in combination with the compound of the present invention include thyroid receptor ligands, such as those disclosed in WO97/21993 (U. Cal SF), WO99/00353 (KaroBio) and WO00/039077 (KaroBio).

The monoamine reuptake inhibitors which may be optionally employed in combination with compound of the present invention include fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

The anorectic agent which may be optionally employed in combination with the compound of the present invention include topiramate (Johnson & Johnson), dexamphetamine, phentermine, phenylpropanolamine or mazindol.

The aforementioned patents and patent applications are incorporated herein by reference.

The above other therapeutic agents, when employed in combination with the compound of the present invention may be used, for example, in those amounts indicated in the Physicians' Desk Reference, as in the patents set out above or as otherwise determined by one of ordinary skill in the art.

Where the compound of the invention are utilized in combination with one or more other therapeutic agent(s), either concurrently or sequentially, the following combination ratios and dosage ranges are preferred.

Where the other antidiabetic agent is a biguanide, the compound of formula I will be employed in a weight ratio to biguanide within the range from about 0.01:1 to about 100:1, preferably from about 0.1:1 to about 5:1.

The compound of formula I will be employed in a weight ratio to the glucosidase inhibitor within the range from about 0.01:1 to about 100:1, preferably from about 0.5:1 to about 50:1.

The compound of formula I will be employed in a weight ratio to the sulfonyl urea in the range from about 0.01:1 to about 100:1, preferably from about 0.2:1 to about 10:1.

The compound of formula I will be employed in a weight ratio to the thiazolidinedione in an amount within the range from about 0.01:1 to about 100:1, preferably from about 0.2:1 to about 10:1.

Where present, the thiazolidinedione anti-diabetic agent may be employed in amounts within the range from about 0.01 to about 2000 mg/day which may be administered in single or divided doses one to four times per day.

Optionally, the sulfonyl urea and thiazolidinedione may be incorporated in a single tablet with the compound of formula I in amounts of less than about 150 mg.

Where present, metformin or salt thereof may be employed in amounts within the range from about 500 to about 2000 mg per day which may be administered in single or divided doses one to four times daily.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The compound of formula I will be employed in a weight ratio to the meglitinide, PPAR-gamma agonist, PPAR-alpha/gamma dual agonist, PPARdelta agonists, PPARalpha/gamma/delta triple agonist, aP2 inhibitor or other DPP4 inhibitor within the range from about 0.01:1 to about 100:1, preferably from about 0.2:1 to about 10:1.

The compound of formula I of the invention will be generally be employed in a weight ratio to the hypolipidemic agent (were present), within the range from about 500:1 to about 1:500, preferably from about 100:1 to about 1:100.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor in an amount within the range of from about 1 to 2000 mg, and preferably from about 4 to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

The squalene synthetase inhibitor may be employed in dosages in an amount within the range of from about 10 mg to about 2000 mg and preferably from about 25 mg to about 200 mg.

A preferred oral dosage form, such as tablets or capsules will contain the squalene synthetase inhibitor in an amount of from about 10 to about 500 mg, preferably from about 25 to about 200 mg.

The compound of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out a preferred method of the invention for treating any of the diseases disclosed herein, such as diabetes and related diseases, a pharmaceutical composition will be employed containing one or more of the compound of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compound can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 10 to about 500 mg of a compound of formula I. The dose for adults is preferably between 10 and 2,000 mg per day, which can be administered in a single dose or in the form of individual doses from 1-4 times per day.

A typical injectable preparation may be produced by aseptically placing 250 mg of compound of formula I into a vial, aseptically freeze-drying and sealing. For use, the contents of the vial are mixed with 2 mL of physiological saline, to produce an injectable preparation.

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

Biological Evaluation

DPP-4 inhibitory activity of the compounds of the present invention may be determined by use of an in vitro assay system which measures the degree in inhibition of DPP-4-mediated cleavage of an appropriate substrate or pseudosubstrate. Inhibition constants (Ki values) for the DPP-4 inhibitors of the invention may be determined by the method described in the experimental section below.

Cloning, Expression and Purification of Human DPP-4

To generate human DPP-4, PCR (Red-tag polymerase, Sigma) was performed on Human cDNA from placenta (Clontech) using two primers, ACGCCGACGATGAAGACA (SEQ ID NO:1) and AGGTAAAGAGAAACATTGTT (SEQ ID NO:2), based on the nucleotide sequence of the human clone (accession number M74777). PCR products were cloned into the pcDN4/HisMax TOPO vector (Invitrogene). For stable transfection of CHO-DG44 cells, DPP4 was rePCRed using primers GGTACCAGCGCAGAGGCTT (SEQ ID NO:3) and CTCGAGCTAAGGTAAAGAGAACATTG (SEQ ID NO:4) to generate KpnI and XhoI sites. The KpnI and XhoI sites were used to extract the N-terminal His tagged gene. The His tag, which could be cleaved and removed by Enterokinase, was included to allow purification using the TALON affinity column. The gene was then ligated into the KpnI and XhoI sites of the pD16 vector for stable transfection. Stable cell lines were generated by transfecting the expression vector into Chinese hamster ovary (CHO-DG44) cells using electroporation. The CHO-DG44 cell line was grown in PFCHO media supplemented with HT (glycine, hypoxanthine and thymidine, Invitrogene), glutamine and Recombulin (ICN). Then 1×107 cells/ml were collected, transfected with 60 µg of DNA using electroporation at 300V, and then transferred to a T75 flask. On the third day following transfection, the HT supplement was removed and selection was initiated with methotrexate (MTX, 10 nM, ICN). After a further 10 days the cells were plated into individual wells of 96 well plates. Every 10 days the concentration of MTX was increased two to three fold, up to a maximum of 400 nM. Final stable cell line selection was based on yield and activity of the expressed protein.

An attempt to purify recombinant DPP-4 using Talon resin was not efficient, resulting in small yields, with most of the DPP activity passing through the column. Therefore, protein was further purified using conventional anion exchange (Sepharose Q), gel filtration (S-200) and high resolution MonoQ columns. The final protein yielded a single band on SDS-PAGE gels. Amino acid sequence analysis indicated two populations of DPP-4 in the sample. One portion of the protein had 27 amino acids truncated from the N-terminus, while the other was lacking the N-terminal 37 amino acids. This suggests that during isolation the entire transmembrane domain (including His tag) is removed by proteases present in the CHO cells. Total protein concentration was measured using the Bradford dye method and the amount of the active DPP-4 was determined by titrating the enzyme with a previously characterized inhibitor (Ki=0.4 nM). No biphasic behavior was observed during inhibition or catalysis, suggesting that both protein populations are functionally identical.

DPP-4 Inhibition Assays

Inhibition of human DPP-4 activity was measured under steady-state conditions by following the absorbance increase at 405 nm upon the cleavage of the pseudosubstrate, Gly-Pro-pNA. Assays were performed in 96-well plates using a Thermomax plate reader. Typically reactions contained 100 μl of ATE buffer (100 mM Aces, 52 mM Tris, 52 mM ethanolamine, pH 7.4), 0.45 nM enzyme, either 120 or 1000 μM of substrate (S<Km and S>Km, Km=180 μM) and variable concentration of the inhibitor. To ensure steady-state conditions for slow-binding inhibitors, enzyme was preincubated with the compound for 40 minutes prior to substrate addition, to initiate the reaction. All serial inhibitor dilutions were in DMSO and final solvent concentration did not exceed 1%.

Inhibitor potency was evaluated by fitting inhibition data to the binding isotherm:

$$\frac{vi}{v} = \frac{\text{Range}}{1 + \left(\frac{I}{IC_{50}}\right)^n} + \text{Background} \quad (1)$$

where vi is the initial reaction velocity at different concentrations of inhibitor I; v is the control velocity in the absence of inhibitor, range is the difference between the uninhibited velocity and background; background is the rate of spontaneous substrate hydrolysis in the absent of enzyme, n is the Hill coefficient.

Calculated $IC_{50}$s at each substrate concentration were converted to Ki assuming competitive inhibition according to:

$$Ki = \frac{IC_{50}}{\left(1 + \frac{S}{Km}\right)} \quad (2)$$

All inhibitors were competitive as judged by a very good agreement of Ki values obtained from the assays at high and low substrate concentrations. In cases where $IC_{50}$ at the low substrate concentration was close to the enzyme concentration used in the assay, the data were fit to the Morrison equation[1], to account for the depletion of the free inhibitor:

$$\frac{vi}{v0} = 1 - \frac{(E + I + IC_{50}) - \sqrt{(E + I + IC_{50})^2 - 4EI}}{2E} \quad (3)$$

where vi and v0 are the steady state velocities measured in the presence and absence of inhibitor, E enzyme concentration.

[1] Morrison, J. F., Walsh, C. T., *Advances in Enzymology*, 61:201-206 (1988).

Each $IC_{50}$ was further refined to Ki, to account for the substrate concentration in the assay using equation (2).

ABBREVIATIONS

The following abbreviations are employed in the Examples and elsewhere herein:

Ph=phenyl

Bn=benzyl i-Bu=iso-butyl

Me=methyl

Et=ethyl

Pr=propyl

Bu=butyl

Boc or BOC=tert-butoxycarbonyl

Cbz=carbobenzyloxy or carbobenzoxy or benzyloxycarbonyl

HOAc or AcOH=acetic acid

DMF=N,N-dimethylformamide

DMSO=dimethylsulfoxide

EtOAc=ethyl acetate

Hex=hexanes $CHCl_3$=chloroform $CH_2Cl_2$=dichloromethane

THF=tetrahydrofuran

TFA=trifluoroacetic acid

Pd/C=palladium on carbon $LiBH_4$=lithium borohydride $NaBH_4$=sodium borohydride MsCl=methanesulfonyl chloride DIBAL-H=diisobutylaluminum hydride TEA=triethylamine min=minute(s)

h or hr=hour(s)

L=liter mL=milliliter

μL=microliter g=gram(s)

mg=milligram(s)

mol=mole(s)

mmol=millimole(s)

meq=milliequivalent rt=room temperature sat or sat'd=saturated aq.=aqueous

TLC=thin layer chromatography $R_f$=retention time mp=melting point

HPLC=high performance liquid chromatography

PrepHPLC=preparative HPLC

Solvent A (Prep HPLC): 90% $H_2O$/10% MeOH+0.1% TFA

Solvent B (Prep HPLC): 90% MeOH/10% $H_2O$+0.1% TFA

LC/MS=high performance liquid chromatography/mass spectrometry

MS or Mass Spec=mass spectrometry

HRMS=high resolution mass spectrometry

NMR=nuclear magnetic resonance equiv=equivalent(s)

EXAMPLES

The following examples are provided to describe the invention in further detail. These examples, which set forth the best mode presently contemplated for carrying out the invention, are intended to illustrate and not to limit the invention.

In general, preferred compounds of the present invention, such as the particular compounds disclosed in the following examples, have been identified to inhibit the catalytic activity of dipeptidyl peptidase IV at concentrations equivalent to, or more potently than, 10 μM, preferably 5 μM, more preferably 3 μM, thereby demonstrating that the compounds of the present invention possess utility as effective inhibitors of dipeptidyl peptidase IV. Potencies can be calculated and expressed as either inhibition constants (Ki values) or as $IC_{50}$ (inhibitory concentration 50%) values, and refer to activity measured employing the in vitro assay system described herein.

Example 1

3-(Aminomethyl)-4-(2,4-dichlorophenyl)-2-methyl-7,8-dihydro-1,6-naphthyridin-5(6H)-one HCl salt

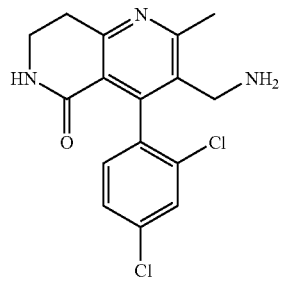

Example 1A (Z)-Benzyl 3-aminobut-2-enoate

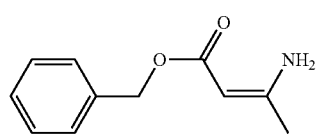

A mixture of benzyl acetoacetate (4.6 g, 24 mmol) and ammonium acetate (9.2 g, 119.5 mmol) in methanol (30 mL) was allowed to stir at ambient temperature for 72 h. The solvent was evaporated, and the residue was taken up in $CHCl_3/H_2O$. The combined organic layers were washed with brine, dried ($Na_2SO_4$), and evaporated to give Example 1A (4.3 g, 90% yield) as a golden oil. $^1H$ NMR (400 MHz, $CDCl_3$) δ1.91 (s, 3H), 4.60 (s, 1H), 5.12 (s, 2H), 7.24-7.40 (m, 5H).

Example 1B (Z)-Ethyl 2-(2,4-dichlorobenzylidene)-4-chloro-3-oxobutanoate

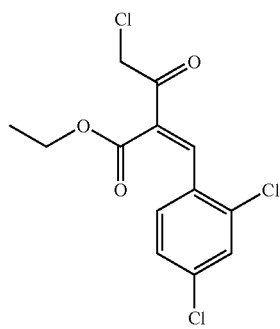

A solution 2,4-dichlorobenzaldehyde (4.6 g, 26.1 mmol), ethyl 4-chloro-3-oxobutanoate (4.5 g, 27.4 mmol), benzylamine (165 mg, 1.5 mmol), and acetic acid (118 mg, 2.0 mmol) in isopropyl alcohol (30 mL) stirred at ambient temperature for 96 h. The mixture was diluted with isopropyl alcohol to give a total volume of 50 mL and was saved as a stock solution of Example 1B (0.52 mmol/mL).

Example 1C

3-Benzyl 5-ethyl 6-(chloromethyl)-4-(2,4-dichlorophenyl)-2-methyl-1,4-dihydropyridine-3,5-dicarboxylate

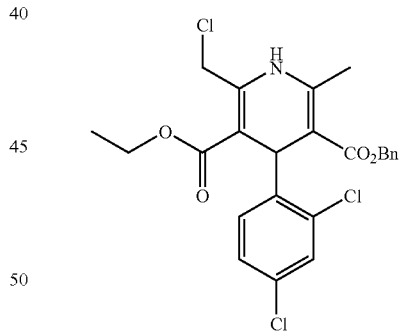

A mixture of stock solution of Example 1B (25 mL, 13 mmol) and Example 1A (2.8 g, 14.5 mmol) in isopropyl alcohol (3 mL) was allowed to stir at ambient temperature for 18 h. The reaction was quenched with concentrated HCl (8 mL), and the mixture stirred at ambient temperature for 2 h. The reaction was concentrated in vacuo, diluted with diethyl ether, filtered and evaporated. The residue was purified by flash chromatography (120 g column, EtOAc/Hexanes) to give Example 1C (4.2 g, 65% yield) as a yellow, sticky oil. $^1H$ NMR (400 MHz, $CDCl_3$) δ 1.19 (t, J=7.0 Hz, 3H), 2.35 (s, 3H), 4.05-4.15 (m, 2H), 4.82 and 4.97 ($AB_q$, J=14.1 Hz, 2H), 5.07 and 5.11 ($AB_q$, J=12.3 Hz, 2H), 5.41 (s, 1H), 6.37 (broad s, 1H), 7.07 (dd, J=8.4, 2.2 Hz, 1H), 7.16-7.32 (m, 5H), 7.35-7.38 (m, 2H).

Example 1D

3-Benzyl 5-ethyl 6-(chloromethyl)-4-(2,4-dichlorophenyl)-2-methylpyridine-3,5-dicarboxylate

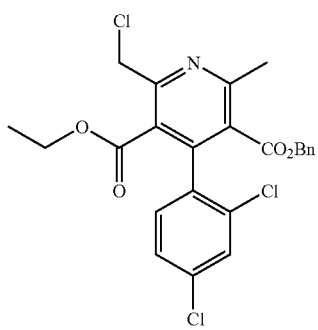

Example 1C (4.1 mg, 8.2 mmol) was dissolved in acetic acid (30 mL) and 70% nitric acid/water (25 mL). The reaction mixture was allowed to stir at ambient temperature for 18 h. The crude product (4.2 g) was purified by flash chromatography (120 g column, 0-100% EtOAc/Hex) to give Example 1D (2.7 g, 68% yield) as a pale yellow oil. $^1$H NMR (400 MHz, CDCl$_3$) δ 0.98 (t, J=7.3 Hz, 3H), 2.65 (s, 3H), 4.05 (q, J=7.0 Hz, 2H), 4.77 and 4.92 (AB$_q$, J=11.0 Hz, 2H), 5.04 (s, 2H), 7.01 (d, J=8.35 Hz, 1H), 7.07 (dd, J=8.4, 2.2 Hz, 1H), 7.10-7.14 (m, 2H), 7.21 (d, J=2.2 Hz, 1H), 7.28-7.28 (m, 3H). [M+H]$^+$=491.98.

Example 1E

3-Benzyl 5-ethyl 6-(cyanomethyl)-4-(2,4-dichlorophenyl)-2-methylpyridine-3,5-dicarboxylate

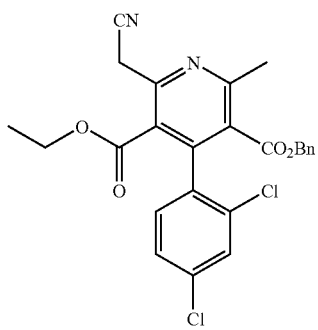

A suspension of Example 1D (980 mg, 2.0 mmol) and KCN (143 mg, 2.2 mmol) in 20 ml of Ethanol/water (2:1) was heated at reflux until HPLC indicated that the starting material was completely consumed. The reaction was diluted with ethyl acetate, washed with water and brine, dried (MgSO$_4$) and concentrated. The residue was purified by flash chromatography (elution with 1:4 EtOAc/hexane) to afford 656 mg (59%) of Example 1E as a solid. $^1$H NMR (500 MHz, CDCl$_3$) δ 0.92 (t, 3H), 2.66 (s, 3H), 4.04 (m, 2H), 4.14 (d, 2H), 5.02 (s, 2H), 6.99 (d, 1H), 7.09 (d, 1H), 7.13 (d, 2H), 7.21 (s, 1H), 7.31 (m, 3H). LRMS (ESI): 483.2/485.1 [M+H]$^+$.

Example 1F 6-(2-Aminoethyl)-4-(2,4-dichlorophenyl)-5-(ethoxycarbonyl)-2-methylnicotinic acid

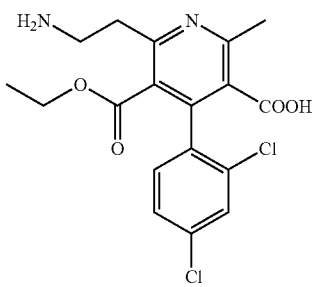

A mixture of Example 1E (1.06 g, 2.2 mmol), 10% Pd/C (424 mg) and 2 drops of concentrated HCl aq. solution in 40 mL of methanol was stirred under H$_2$ (1 atm, maintained by balloon) overnight at ambient temperature. The mixture was filtered through a pad of Celite and concentrated. The residue was purified by flash chromatography (elution with 1:5 MeOH/1,2-dichloromethane) to afford 540 mg (62%) of Example 1F as an solid. LRMS (ESI): 397.1/399.0 [M+H]$^+$.

Example 1G 4-(2,4-Dichlorophenyl)-2-methyl-5-oxo-5,6,7,8-tetrahydro-1,6-naphthyridine-3-carboxylic acid

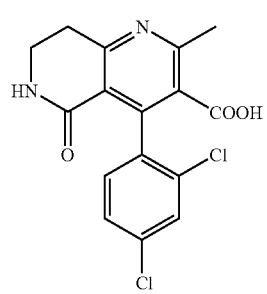

A mixture of Example 1F (540 mg, 1.36 mmol) and t-BuONa (197 mg, 2.05 mmol) was irradiated in a sealed tube in a microwave reactor at 120° C. for 20 min. The volatiles were removed in vacuo. The crude product was purified by flash chromatography (elution with 0-20% MeOH/CH$_2$Cl$_2$) to afford 412 mg (87%) of Example 1G as a solid. LRMS (ESI): 351.0/353.0 [M+H]$^+$.

Example 1H 4-(2,4-Dichlorophenyl)-3-(hydroxymethyl)-2-methyl-7,8-dihydro-1,6-naphthyridin-5(6H)-one

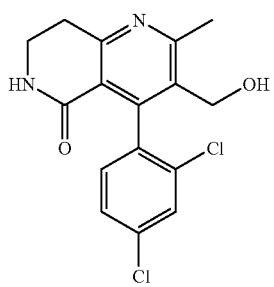

To a mixture of Example 1G (412 mg, 1.18 mmol) and triethylamine (0.20 ml, 1.41 mmol) in THF (10 mL) was added ethyl chloroformate (153 mg, 1.41 mmol) dropwise at 0° C. The reaction mixture was stirred for 10 min. To the reaction mixture, NaBH4 (445 mg, 11.8 mmol) in 5 mL of water was added at 0° C. The reaction was stirred for 15 min. The reaction was quenched with 1M HCl aq solution. The reaction was diluted with ethyl acetate, washed with water and brine, dried (MgSO$_4$) and concentrated to afford 395 mg of crude Example 1H as a solid. LRMS (ESI): 337.1/339.1 [M+H]$^+$.

Example 1I 3-(Chloromethyl)-4-(2,4-dichlorophenyl)-2-methyl-7,8-dihydro-1,6-naphthyridin-5(6H)-one

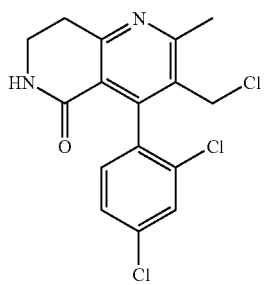

To a solution of Example 1H (395 mg, 1.18 mmol) and triethylamine (1.3 ml, 9.4 mmol) in THF (20 mL) was added mesyl chloride (1.0 g, 9.4 mmol) dropwise. The reaction mixture was allowed to stir at ambient temperature overnight. The volatiles were removed in vacuo. The crude product was purified by flash chromatography (elution with 0-100% EtOAc/hexane to afford 302 mg (72% for 2 steps) of Example 1I as a solid. LRMS (ESI): 355.1/357.1 [M+H]$^+$.

Example 1

3-(Aminomethyl)-4-(2,4-dichlorophenyl)-2-methyl-7,8-dihydro-1,6-naphthyridin-5(6H)-one, HCl salt A suspension of Example 1I (150 mg, 0.42 mmol) in 5 mL of Ammonia (2M in MeOH) was irradiated in a sealed tube in a microwave reactor at 120° C. for 20 min. The volatiles were removed in vacuo. The crude product was purified by flash chromatography (elution with 0-20% MeOH/CH$_2$Cl$_2$) to afford an oil, which was treated with 4M HCl in MeOH to yield 32 mg (21%) of Example 1 as a solid. $^1$H NMR (500 MHz, DMSO-D$_6$): δ 8.46 (s, 2H), 8.06 (s, 1H), 7.68 (d, J=4.3 Hz, 1H), 7.47 (dd, J=10.9, 5.5 Hz, 1H), 7.38 (t, 1H), 3.99 (m, 1H), 3.50-3.35 (m, 3H), 3.20-3.14 (m, 2H), 2.79 (s, 3H). LRMS (ESI): 336.1/338.1 [M+H]$^+$.

Example 2 and Example 3

(S)-2-(3-(Aminomethyl)-4-(2,4-dichlorophenyl)-2-methyl-5-oxo-7,8-dihydro-1,6-naphthyridin-6(5H)-yl)-N,N-dimethylacetamide TFA salt (Example 2), and (S)-2-(3-(Aminomethyl)-4-(2-chlorophenyl)-2-methyl-5-oxo-7,8-dihydro-1,6-naphthyridin-6(5H)-yl)-N,N-dimethylacetamide TFA salt (Example 3)

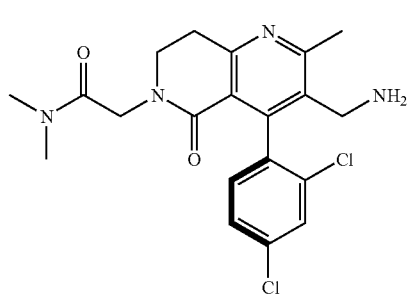

Example 2

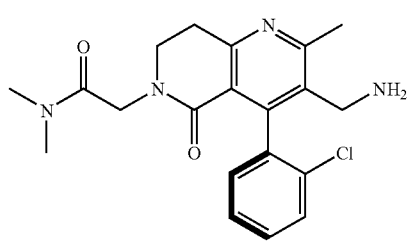

Example 3

Example 2A

Methyl 5-cyano-4-(2,4-dichlorophenyl)-2-(2-methoxyethyl)-6-methyl-1,4-dihydropyridine-3-carboxylate

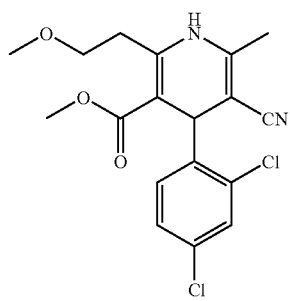

A solution of 2,4-dichlorobenzaldehyde (16.5 g, 94.3 mmol), methyl 5-methoxy-3-oxopentanoate (15.1 g, 94.3 mmol), piperidine (480 mg, 5.7 mmol), and acetic acid (340 mg, 5.7 mmol) in MeOH (80 mL) was stirred at ambient temperature overnight. To the reaction mixture, 3-aminocrotonitrile (7.74 g, 94.3 mmol) in 30 ml of methanol was added. The resulting solution was stirred at ambient temperature overnight. The reaction was quenched with concentrated HCl (4 mL), and stirred at ambient temperature for 2 h. The reaction was filtered, the solid was washed with hexane and the mother liquid was concentrated and purified by flash chromatography (elution with 0-50% EtOAc/hexane), combined with the filtrate, to afford 33.1 g (92%) of Example 2A as a solid. LRMS (ESI): 381.3 [M+H]+.

Example 2B

Methyl 5-cyano-4-(2,4-dichlorophenyl)-2-(2-methoxyethyl)-6-methylnicotinate

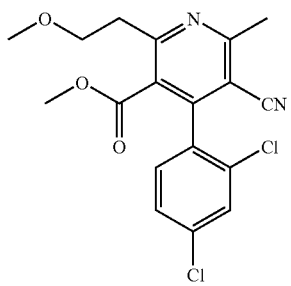

Example 2A (33.1 g, 87.1 mmol) was dissolved in acetonitrile (150 mL) and 70% nitric acid (30 mL). The reaction mixture was allowed to stir at ambient temperature for 30 min. The reaction was diluted with EtOAc, washed with water and brine, dried over MgSO$_4$ and concentrated in vacuo. The residue was purified by flash chromatography (elution with 0-20% EtOAc/hexane) to afford 31.8 g (74%) of Example 2B as an oil. $^1$H NMR (500 MHz, CDCl$_3$) δ7.54 (s, 1H), 7.35 (d, 1H), 7.16 (d, 1H), 3.78-3.86 (m, 2H), 3.59 (s, 3H), 3.34 (s, 3H), 2.20-2.60 (m, 2H), 2.84 (s, 3H). LRMS (ESI): 379.2/381.2 [M+H]+.

Example 2C

Methyl 5-cyano-4-(2,4-dichlorophenyl)-2-(2-hydroxyethyl)-6-methylnicotinate

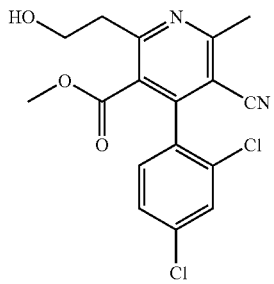

To Example 2B (6.76 g, 17.9 mmol) in 350 mL of CH$_2$Cl$_2$, BBr$_3$ (1M in CH$_2$Cl$_2$, 18.8 mmol) was added dropwise at 0° C. After the addition, the reaction was stirred at ambient temperature for 60 min. The reaction was washed with water and brine, dried (MgSO$_4$) and concentrated. The residue was purified by flash chromatography (elution with 0-100% EtOAc/hexane) to afford 4.68 g (72%) of Example 2C as an oil. $^1$H NMR (500 MHz, CDCl$_3$) δ7.56 (s, 1H), 7.36 (d, 1H), 7.16 (d, 1H), 4.08 (m, 2H), 3.60 (s, 3H), 3.17 (m, 2H), 2.86 (s, 3H). LRMS (ESI): 365.1/367.1 [M+H]+.

Example 2D 4-(2,4-Dichlorophenyl)-2-methyl-5-oxo-5,6,7,8-tetrahydro-1,6-naphthyridine-3-carbonitrile

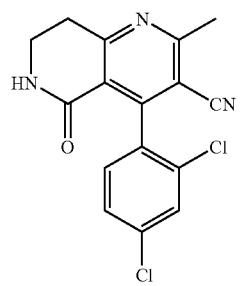

A suspension of Example 2C (1.34 g, 6.42 mmol) in 8 mL of ammonium hydroxide and 15 mL of MeOH was irradiated in a sealed tube in a microwave reactor at 150° C. for 2.5 h. The reaction was diluted with EtOAc and washed with water and brine, dried (MgSO$_4$) and concentrated. The residue was purified by flash chromatography (elution with 0-10% MeOH/CH$_2$Cl$_2$) to afford 1.42 g (66%) of Example 2D as a solid. $^1$H NMR (500 MHz, CDCl$_3$) δ7.50 (s, 1H), 7.38 (d, 1H), 7.17 (d, 1H), 6.44 (broad s, 1H), 3.62-3.50 (m, 2H), 3.30-3.20 (m, 2H), 2.86 (s, 3H). LRMS (ESI): 332.1/334.1 [M+H]+.

Example 2E 2-(3-Cyano-4-(2,4-dichlorophenyl)-2-methyl-5-oxo-7,8-dihydro-1,6-naphthyridin-6(5H)-yl)-N,N-dimethylacetamide

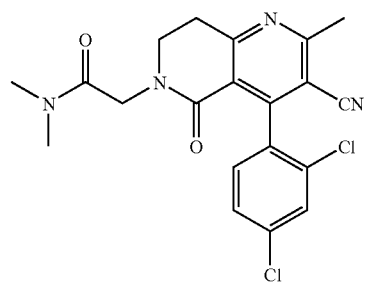

To a suspension of NaH (60% in oil, 256 mg, 6.4 mmol) in 10 mL of DMF at 0° C. was added Example 2D (1.06 g, 3.2 mmol) dropwise in 30 mL of DMF. After the addition, the reaction was stirred for 10 min. Then there was added 2-chloro-N,N-dimethylacetamide (0.78 g, 6.4 mmol), and the reaction was stirred at room temperature for 3 h. The reaction was diluted with EtOAc, washed with water and brine, dried (MgSO$_4$) and concentrated. The residue was purified by flash chromatography (elution with 0-100% EtOAc/hexane) to afford 695 mg (72%) of Example 2E as an oil. $^1$H NMR (500 MHz, CDCl$_3$) δ7.49 (s, 1H), 7.37 (d, 1H), 7.16 (d, 1H), 4.50 and 4.10 (ABq, 2H), 3.76-3.70 (m, 2H), 3.46-3.32 (m, 2H), 2.95 (s, 3H), 2.93 (s, 3H), 2.85 (s, 3H). LRMS (ESI): 417.2 [M+H]$^+$.

Example 2F

Chiral separation of 2-(3-cyano-4-(2,4-dichlorophenyl)-2-methyl-5-oxo-7,8-dihydro-1,6-naphthyridin-6(5H)-yl)-N,N-dimethylacetamide into individual atropisomers

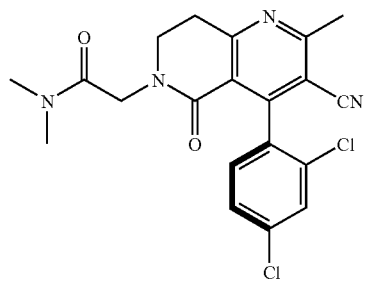

Atropisomer 2F-1
Fast-moving

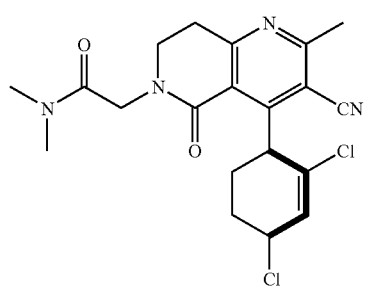

Atropisomer 2F-2
Slow-moving

A 695 mg sample of racemic Example 2E was separated by chiral HPLC (Chiralcel OJ column, 20μ, 5×50 cm column, elution with 0-80% i-PrOH/heptane) to afford the two individual atropisomers.

Example 2F-1

Atropisomer 1; Faster-Moving 293 mg, purity by chiral analytical HPLC [Chiralcel OJ 4.6×250 mm; 20% i-PrOH/heptane, retention time 6.5 min]: >99% ee. LRMS (ESI): 417.2 [M+H]$^+$.

Example 2F-2

Atropisomer 2; Slower-Moving 332 mg, purity by chiral analytical HPLC [Chiralcel OD 4.6×250 mm; 20% i-PrOH/heptane, retention time 11.0 min]: >99% ee. LRMS (ESI): 417.2 [M+H]$^+$.

Example 2 and Example 3

(S)-2-(3-(Aminomethyl)-4-(2,4-dichlorophenyl)-2-methyl-5-oxo-7,8-dihydro-1,6-naphthyridin-6(5H)-yl)-N,N-dimethylacetamide TFA salt (Example 2), and (S)-2-(3-(Aminomethyl)-4-(2-chlorophenyl)-2-methyl-5-oxo-7,8-dihydro-1,6-naphthyridin-6(5H)-yl)-N,N-dimethylacetamide TFA salt (Example 3)

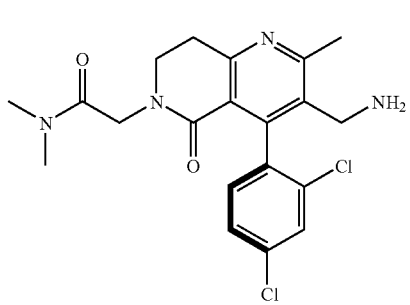

Example 2

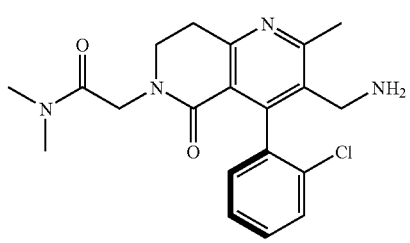

Example 3

A suspension of Example 2F-1, the faster-moving atropisomer, (293 mg, 0.70 mmol) and wet RaNi (Grade 2400, ~150 mg) in 15 mL of MeOH was stirred under H$_2$ (1 atm, maintained by balloon) overnight at ambient temperature. The reaction was filtered through Celite and concentrated, the residue was purified by prep HPLC (Phenomenex, 10 min gradient, 20 to 100% B) and lyophilized to dryness overnight to afford 44 mg of Example 2 as a TFA salt. $^1$H NMR (500 MHz, CD$_3$OD) δ7.60 (d, 1H, J=2.2 Hz), 7.42 (dd, 1H, J=9.4, 2.2 Hz), 7.18 (d, 1H, J=8.3 Hz), 4.40 and 4.20 (ABq, 2H, J$_{AB}$=16.7 Hz), 4.07 and 3.78 (ABq, 2H, J$_{AB}$=14.5 Hz), 3.75-3.60 (m, 2H), 3.40-3.20 (m, 2H), 3.00 (s, 3H), 2.91 (s, 3H), 2.76 (s, 3H). LRMS (ESI): 421.2 [M+H]$^+$.

There was also isolated 43 mg of Example 3 as a TFA salt. $^1$H NMR (500 MHz, CD$_3$OD) δ7.51 (d, 1H, J=8.2 Hz), 7.45-7.38 (m, 2H), 7.20 (d, 1H, J=7.7 Hz), 4.38 and 4.20 (ABq, 2H, J$_{AB}$=16.7 Hz), 4.08 and 3.77 (ABq, 2H, J$_{AB}$=14.8 Hz), 3.75-

3.60 (m, 2H), 3.40-3.20 (m, 2H), 3.00 (s, 3H), 2.91 (s, 3H), 2.77 (s, 3H). LRMS (ESI): 387.2 [M+H]⁺.

Example 4 and Example 5

(R)-2-(3-(Aminomethyl)-4-(2,4-dichlorophenyl)-2-methyl-5-oxo-7,8-dihydro-1,6-naphthyridin-6(5H)-yl)-N,N-dimethylacetamide TFA salt (Example 4), and (R)-2-(3-(Aminomethyl)-4-(2-chlorophenyl)-2-methyl-5-oxo-7,8-dihydro-1,6-naphthyridin-6(5H)-yl)-N,N-dimethylacetamide TFA Salt (Example 5)

Example 4

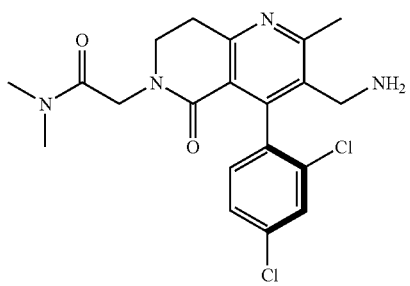

Example 5

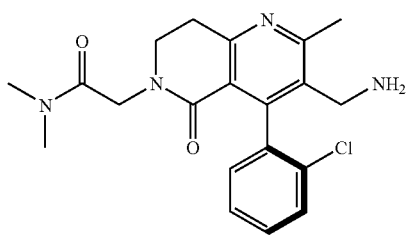

Example 4 and Example 5 were prepared using the same method described above for Example 2 and Example 3 with the exception that starting material Example 2F-1 was replaced with the slower-moving atropisomer, Example 2F-2.

Example 4

¹H NMR (500 MHz, CD₃OD) δ7.60 (d, 1H, J=2.2 Hz), 7.42 (dd, 1H, J=9.4, 2.2 Hz), 7.18 (d, 1H, J=8.3 Hz), 4.40 and 4.20 (ABq, 2H, J$_{AB}$=16.7 Hz), 4.07 and 3.78 (ABq, 2H, J$_{AB}$=14.5 Hz), 3.75-3.60 (m, 2H), 3.40-3.20 (m, 2H), 3.00 (s, 3H), 2.91 (s, 3H), 2.76 (s, 3H). LRMS (ESI): 421.2 [M+H]⁺.

Example 5

¹H NMR (500 MHz, CD₃OD) δ7.51 (d, 1H, J=8.2 Hz), 7.45-7.38 (m, 2H), 7.20 (d, 1H, J=7.7 Hz), 4.38 and 4.20 (ABq, 2H, J$_{AB}$=16.7 Hz), 4.08 and 3.77 (ABq, 2H, J$_{AB}$=14.8 Hz), 3.75-3.60 (m, 2H), 3.40-3.20 (m, 2H), 3.00 (s, 3H), 2.91 (s, 3H), 2.77 (s, 3H). LRMS (ESI): 387.2 [M+H]⁺.

Example 6

(S)-2-(3-(Aminomethyl)-4-(2,4-dichlorophenyl)-2-methyl-5-oxo-7,8-dihydro-1,6-naphthyridin-6(5H)-yl)acetamide TFA salt

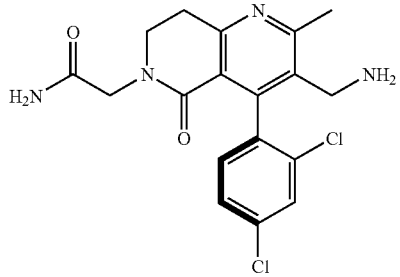

Example 6A

Methyl 5-cyano-4-(2,4-dichlorophenyl)-6-methyl-2-vinylnicotinate

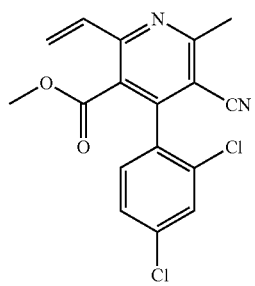

To Example 2C (7.85 g, 21.56 mmol) and triethylamine (5.0 ml, 32.3 mmol) in 220 mL of CH₂Cl₂, methanesulfonyl chloride (1.8 mL, 23.7 mmol) was added dropwise at 0° C. After the addition, the reaction was refluxed for 30 min. The reaction was concentrated. The residue was purified by flash chromatography (elution with 0-10% EtOAc/hexane) to afford 5.35 g (72%) of Example 6A as a solid. ¹H NMR (500 MHz, CDCl₃) δ7.55 (s, 1H), 7.38 (d, 1H), 7.17 (d, 1H), 6.95-6.86 (dd, 1H), 6.74 (d, 1H), 5.76 (d, 1H), 3.61 (s, 3H), 2.86 (s, 3H). LRMS (ESI): 347.1/349.1 [M+H]⁺.

Example 6B 2-(3-Cyano-4-(2,4-dichlorophenyl)-2-methyl-5-oxo-7,8-dihydro-1,6-naphthyridin-6(5H)-yl)acetic acid

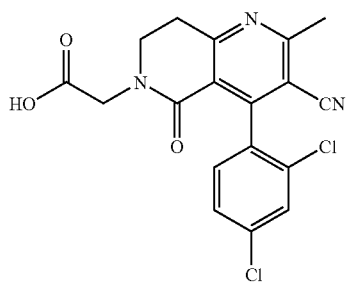

A mixture of Example 6A (2.65 g, 7.66 mmol), glycine (0.63 g, 8.42 mmol) and Hunig's base (1.1 g, 8.42 mmol) in 20 ml of MeOH/MeCN (1:1) was irradiated in a sealed tube in a microwave reactor at 150° C. for 30 min. The volatiles were removed in vacuo. The residue was purified by flash chromatography (elution with 0-15% MeOH/CH$_2$Cl$_2$) to afford 2.48 g (83%) of Example 6B as a foam. $^1$H NMR (500 MHz, CDCl$_3$) δ7.47 (s, 1H), 7.31 (d, 1H), 7.13 (d, 1H), 4.20 and 4.00 (ABq, 2H), 3.76-3.70 (m, 2H), 3.35-3.28 (m, 2H), 2.84 (s, 3H). LRMS (ESI): 390.1/392.1 [M+H]$^+$.

Example 6C

Chiral separation of 2-(3-cyano-4-(2,4-dichlorophenyl)-2-methyl-5-oxo-7,8-dihydro-1,6-naphthyridin-6(5H)-yl)acetic acid into individual atropisomers

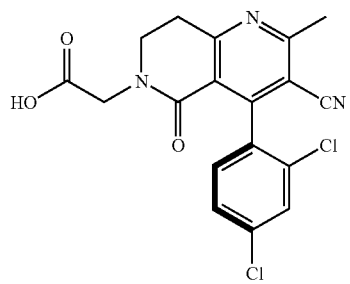

Atropisomer 6C-1
Fast-moving

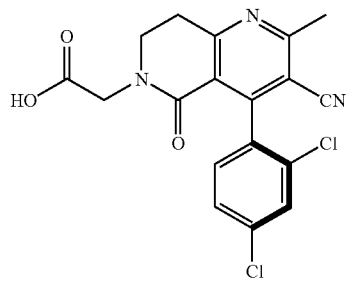

Atropisomer 6C-2
Slow-moving

A 4.96 g sample of racemic Example 6B was separated by chiral HPLC (Chiralcel OJ column, 20μ, 5×50 cm column, elution with 0-80% i-PrOH/heptane) to afford the two individual atropisomers.

Example 6C-1

Atropisomer 1; Faster-Moving 1.92 g, purity by chiral analytical HPLC [Chiralcel OJ 4.6×250 mm; 40% i-PrOH/heptane, retention time 6.5 min]: >99% ee. LRMS (ESI): 390.1/392.1 [M+H]$^+$.

Example 6C-2

Atropisomer 2; Slower-Moving 2.09 g, purity by chiral analytical HPLC [Chiralcel OJ 4.6×250 mm; 40% i-PrOH heptane, retention time 11.0 min]: >99% ee. LRMS (ESI): 390.1/392.1 [M+H]$^+$.

Example 6

(S)-2-(3-(Aminomethyl)-4-(2,4-dichlorophenyl)-2-methyl-5-oxo-7,8-dihydro-1,6-naphthyridin-6(5H)-yl)acetamide TFA salt

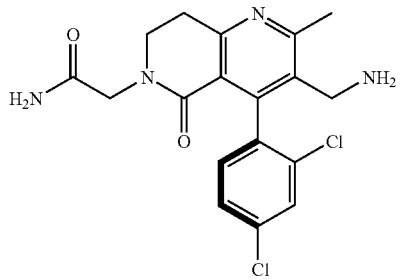

A mixture of Example 6C-1, the fast-moving atropisomer, (98 mg, 0.25 mmol), 1-hydroxybenzotriazole (41 mg, 0.30 mmol) and EDC (58 mg, 0.30 mmol), in 2 ml of 4M NH$_3$ in MeOH was stirred at ambient temperature for 2 h. The volatiles were removed in vacuo. The residue was purified by flash chromatography (elution with 0-10% MeOH/CH$_2$Cl$_2$) to afford an oil (82 mg), which was dissolved in 20 mL of MeOH in a thick-walled test tube with screw cap, wet RaNi (~500 mg, 2400 grade in water), was added followed by hydrazine (117 μL, 3.7 mmol). The tube was tightly capped. The mixture was allowed to stir at ambient temperature for 1 h. The mixture was filtered through a pad of Celite and concentrated, the residue was purified by prep HPLC (Phenomenex, 10 min gradient, 20 to 100% B) and lyophilized to dryness overnight to afford 64 mg (50%) of Example 6 as a TFA salt. $^1$H NMR (500 MHz, CDCl$_3$) δ7.60 (d, 1H, J=2.2 Hz), 7.42 (dd, 1H, J=1.7, 8.2 Hz), 7.18 (d, 1H, J=8.2 Hz), 4.18 and 4.02 (ABq, 2H, J$_{AB}$=16.5 Hz), 4.07 and 3.79 (ABq, 2H, J$_{AB}$=14.3 Hz), 3.77-3.72 (m, 1H), 3.70-3.65 (m, 1H), 3.36-3.22 (m, 2H), 2.77 (s, 3H). LRMS (ESI): 393.1/395.1 [M+H]$^+$.

Example 7

(S)-2-(3-(Aminomethyl)-4-(2,4-dichlorophenyl)-2-methyl-5-oxo-7,8-dihydro-1,6-naphthyridin-6(5H)-yl)-N-methylacetamide TFA salt

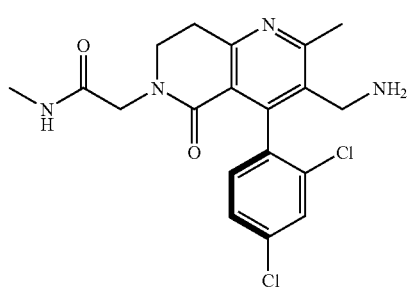

Example 7 was prepared from Example 6C-1, the fast-moving atropisomer, using the same method described above for Example 6 with the exception that ammonia was replaced with methylamine. $^1$H NMR (500 MHz, CDCl$_3$) δ7.47 (d, 1H, J=2.2 Hz), 7.28 (dd, 1H, J=8.3, 1.7 Hz), 7.09 (d, 1H, J=8.2 Hz), 4.20 (ABq, 2H, J$_{AB}$=17.6 Hz), 3.90 (part of ABq, 1H, J=14.3 Hz), 3.76-3.60 (m, 3H), 3.70 (s, 3H), 3.35-3.20 (m, 2H), 2.68 (s, 3H). LRMS (ESI): 408.1/410.1 [M+H]⁺.

Example 8

(S)-2-(3-(Aminomethyl)-4-(2,4-dichlorophenyl)-2-methyl-5-oxo-7,8-dihydro-1,6-naphthyridin-6(5H)-yl)-N,N-diethylacetamide TFA salt

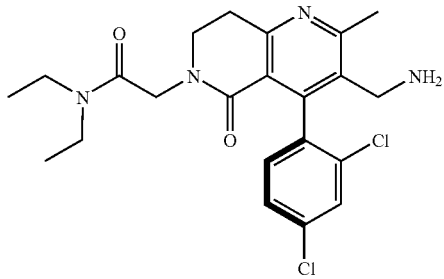

Example 8 was prepared from Example 6C-1, the fast-moving atropisomer, using the same method described above for Example 6 with the exception that ammonia was replaced with diethylamine. ¹H NMR (500 MHz, CD₃OD) δ7.60 (d, 1H, J=2.2 Hz), 7.40 (dd, 1H, J=8.5, 2.2 Hz), 7.18 (dd, 1H, J=8.2, 2.2 Hz), 4.41 and 4.21 (ABq, 2H, J$_{AB}$=16.5 Hz), 4.05 and 3.80 (ABq, 2H, J$_{AB}$=14.3 Hz), 3.80-3.72 (m, 1H), 3.70-3.62 (m, 1H), 3.40-3.20 (overlapping m, 6H), 2.75 (s, 3H), 1.19 (t, 3H), 1.09 (t, 3H). LRMS (ESI): 449.2 [M+H]⁺.

Example 9

(S)-3-(Aminomethyl)-4-(2,4-dichlorophenyl)-2-methyl-6-(2-oxo-2-(pyrrolidin-1-yl)ethyl)-7,8-dihydro-1,6-naphthyridin-5(6H)-one TFA salt

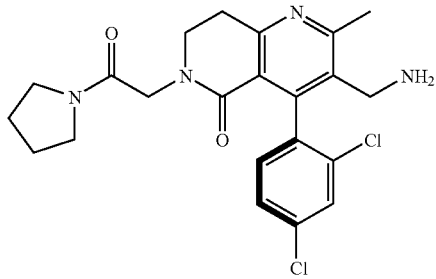

Example 9 was prepared from Example 6C-1, the fast-moving atropisomer, using the same method described above for Example 6 with the exception that ammonia was replaced with pyrrolidine. ¹H NMR (500 MHz, CD₃OD) δ7.57 (d, 1H, J=2.2 Hz), 7.40 (dd, 1H, J=8.5, 2.2 Hz), 7.18 (dd, 1H, J=8.2, 2.2 Hz), 4.27 and 4.12 (ABq, 2H, J$_{AB}$=16.8 Hz), 4.07 and 3.78 (ABq, 2H, J$_{AB}$=14.6 Hz), 3.77-3.72 (m, 1H), 3.68-3.62 (m, 1H), 3.45-3.20 (overlapping m, 6H), 2.75 (s, 3H), 1.98-1.92 (m, 2H), 1.86-1.80 (m, 2H). LRMS (ESI): 447.2 [M+H]⁺.

Example 10

(S)-3-(Aminomethyl)-4-(2,4-dichlorophenyl)-2-methyl-6-(2-oxo-2-(piperidin-1-yl)ethyl)-7,8-dihydro-1,6-naphthyridin-5(6H)-one TFA salt

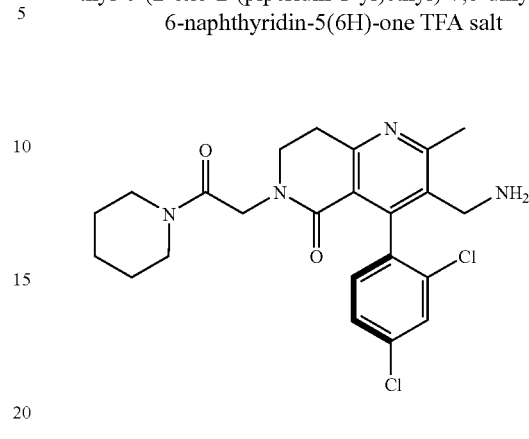

Example 10 was prepared from Example 6C-1, the fast-moving atropisomer, using the same method described above for Example 6 with the exception that ammonia was replaced with piperidine. ¹H NMR (500 MHz, CD₃OD) δ7.59 (d, 1H, J=1.7 Hz), 7.43 (dd, 1H, J=8.2, 2.2 Hz), 7.20 (d, 1H, J=8.2 Hz), 4.38 and 4.23 (ABq, 2H, J$_{AB}$=16.5 Hz), 4.09 and 3.80 (ABq, 2H, J$_{AB}$=14.6 Hz), 3.78-3.72 (m, 1H), 3.67-3.60 (m, 1H), 3.52-3.48 (m, 2H), 3.40-3.22 (overlapping m, 4H), 2.77 (s, 3H), 1.66-1.60 (m, 2H), 1.60-1.55 (m, 2H), 1.55-1.50 (m, 2H). LRMS (ESI): 461.2 [M+H]⁺.

Example 11

(S)-3-(Aminomethyl)-4-(2,4-dichlorophenyl)-2-methyl-6-(2-oxo-2-(2-oxo-1,4'-bipiperidin-1'-yl)ethyl)-7,8-dihydro-1,6-naphthyridin-5(6H)-one TFA salt

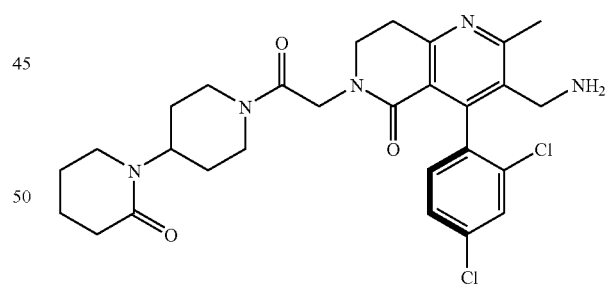

Example 11 was prepared from Example 6C-1, the fast-moving atropisomer, using the same method described above for Example 6 with the exception that ammonia was replaced with 4-(N-delta-valerolactam)piperidine hydrochloride. ¹H NMR (500 MHz, CD₃OD) δ7.59 (d, 1H, J=2.2 Hz), 7.42 (m, 1H), 7.20 (m, 1H), 4.60-4.50 (m, 2H), 4.40-4.28 (m, 1H), 4.15-4.05 (m, 1H), 3.92-3.87 (m, 1H), 3.80-3.70 (overlapping m, 2H), 3.68-3.60 (m, 1H), 3.40-3.20 (overlapping m, 5H), 3.15-3.08 (m, 1H), 2.75 (s, 3H), 2.70-2.65 (m, 1H), 2.38-2.32 (m, 2H), 1.85-1.60 (overlapping m, 8H). LRMS (ESI): 558.4 [M+H]⁺.

Example 12

(S)-3-(Aminomethyl)-4-(2,4-dichlorophenyl)-2-methyl-6-(2-morpholino-2-oxoethyl)-7,8-dihydro-1,6-naphthyridin-5(6H)-one TFA salt

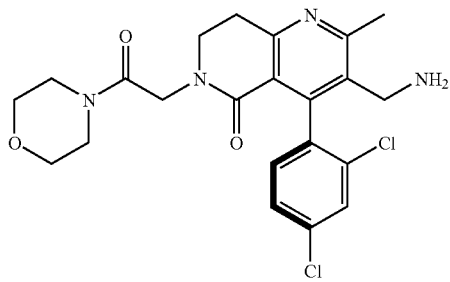

Example 12 was prepared from Example 6C-1, the fast-moving atropisomer, using the same method described above for Example 6 with the exception that ammonia was replaced with morpholine. $^1$H NMR (500 MHz, CD$_3$OD) δ7.59 (d, 1H, J=2.2 Hz), 7.42 (dd, 1H, J=8.2, 1.6 Hz), 7.20 (d, 1H, J=8.3 Hz), 4.37 and 4.22 (ABq, 2H, J$_{AB}$=16.5 Hz), 4.09 and 3.80 (ABq, 2H, J$_{AB}$=14.6 Hz), 3.78-3.72 (m, 1H), 3.68-3.60 (overlapping m, 5H), 3.55-3.50 (m, 2H), 3.48-3.42 (m, 2H), 3.37-3.22 (m, 2H), 2.78 (s, 3H). LRMS (ESI): 463.2 [M+H]$^+$.

Example 13

3-(Aminomethyl)-4-(2,4-dichlorophenyl)-2,6-dimethyl-7,8-dihydro-1,6-naphthyridin-5(6H)-one TFA salt

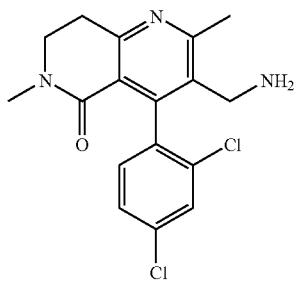

Example 13A 4-(2,4-Dichlorophenyl)-2-methyl-5-oxo-7,8-dihydro-5H-pyrano[4,3-b]pyridine-3-carbonitrile

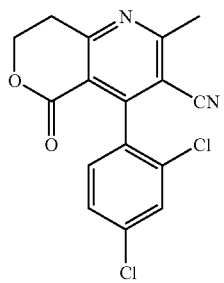

To Example 2B (7.6 g, 20 mmol) in 400 mL of CH$_2$Cl$_2$, BBr$_3$ (20 mL of 1M in CH$_2$Cl$_2$, 20 mmol) was added dropwise at 0° C. After the addition, the reaction was stirred at ambient temperature for 60 min. The reaction was concentrated in vacuo and the residue was purified (ISCO, elution with 0-10% MeOH/CH$_2$Cl$_2$) to afford 6.2 g (92%) of Example 13A as a light brown solid. $^1$H NMR (500 MHz, CDCl$_3$-MIX) δ7.47 (s, 1H), 7.35 (d, 1H), 7.14 (dd, 1H, J=8.3, 1.1 Hz), 4.60-4.50 (m, 2H), 3.31-3.27 (m, 2H), 2.83 (s, 3H). LRMS (ESI): 333.2/335.2 [M+H]$^+$.

Example 13

3-(Aminomethyl)-4-(2,4-dichlorophenyl)-2,6-dimethyl-7,8-dihydro-1,6-naphthyridin-5(6H)-one

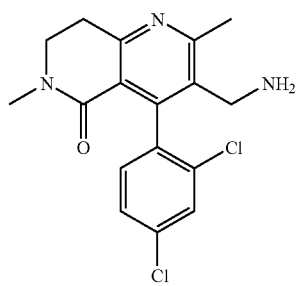

A mixture of Example 13A (120 mg, 0.36 mmol), methylamine (24 g, 0.72 mmol) and Hunig's base (93 mg, 0.72 mmol), in 2 ml of MeOH was irradiated in a sealed tube in a microwave reactor at 150° C. for 60 min. The volatiles were removed in vacuo. The crude product was purified by flash chromatography (elution with 0-15% MeOH/CH$_2$Cl$_2$) to afford an oil, which was dissolved in 10 mL of 2M NH$_3$ in MeOH and hydrogenated under 60 psi with ~200 mg wet RaNi overnight. The mixture was filtered through Celite and concentrated, the residue was purified by prep HPLC (Phenomenex, 10 min gradient, 20 to 100% B) and lyophilized to dryness overnight to afford 14 mg (8% for 2 steps) of Example 13 as a TFA salt. $^1$H NMR (DMSO-D$_6$): δ 7.47 (d, 1H, J=1.7 Hz), 7.27 (d, 2H, J=5.5 Hz), 7.10 (d, 1H, J=8.3 Hz), 3.95 (m, 1H), 3.70-3.55 (m, 3H), 3.30-3.15 (m, 2H), 3.00 (s, 3H), 2.67 (s, 3H). LRMS (ESI): 350.1/352.1 [M+H]$^+$.

Example 14

3-(Aminomethyl)-4-(2,4-dichlorophenyl)-2-methyl-6-(((S)-tetrahydrofuran-2-yl)methyl)-7,8-dihydro-1,6-naphthyridin-5(6H)-one TFA salt

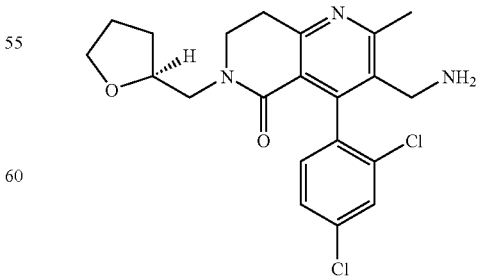

Example 14 was prepared from Example 13A using the same method described above for Example 13 with the exception that methylamine was replaced with (S)-(+)-tetrahydrofurfurylamine. $^1$H NMR (500 MHz, CD$_3$OD) (complex spectra due to mixture of diastereomers): δ7.61 (m, 1H), 7.45 (m, 1H), 7.25 (m, 1H), 4.12-4.02 (overlapping m, 2H), 3.85-3.60 (overlapping m, 6H), 3.35-3.20 (m, 3H), 2.78 (s, 3H), 1.97-1.82 (m, 3H), 1.55-1.50 (m, 1H), LRMS (ESI): 420.3/422.3 [M+H]$^+$.

Example 15

3-(Aminomethyl)-4-(2,4-dichlorophenyl)-6-(2-methoxyethyl)-2-methyl-7,8-dihydro-1,6-naphthyridin-5(6H)-one TFA salt

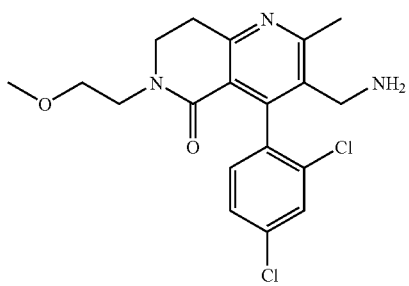

Example 15 was prepared from Example 13A using the same method described above for Example 13 with the exception that methylamine was replaced with 2-methoxyethylamine. $^1$H NMR (500 MHz, CD$_3$OD) δ7.47 (d, 1H, J=2.2 Hz), 7.27 (dd, 1H, J=8.2, 2.2 Hz), 7.07 (d, 1H, J=2.2 Hz), 3.75-3.45 (overlapping m, 8H), 3.31 (s, 3H), 3.20-3.12 (m, 2H), 2.74 (s, 3H). LRMS (ESI): 394.3/396.3 [M+H]$^+$.

Example 16

3-(Aminomethyl)-4-(2,4-dichlorophenyl)-6-(2-hydroxyethyl)-2-methyl-7,8-dihydro-1,6-naphthyridin-5(6H)-one TFA salt

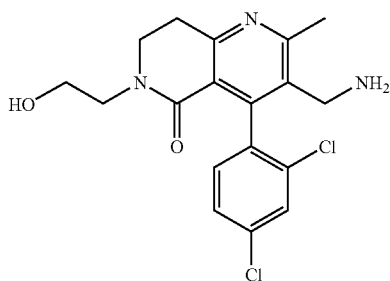

To Example 15 (41 mg, 0.104 mmol) in 2 mL of CH$_2$Cl$_2$, BBr$_3$ (1M in CH$_2$Cl$_2$, 115 uL, 0.11 mmol) was added dropwise at 0° C. After the addition, the reaction was stirred at ambient temperature for 2 h. The reaction was filtered over Celite and concentrated. The residue was purified by prep HPLC (Phenomenex, 10 min gradient, 20 to 100% B) and lyophilized to dryness overnight to afford 11 mg (21%) of Example 16 as a TFA salt. $^1$H NMR (500 MHz, CD$_3$OD) δ7.61 (d, 1H, J=2.2 Hz), 7.45 (dd, 1H, J=8.2, 2.2 Hz), 7.20 (d, 1H, J=8.3 Hz), 4.52-4.48 (m, 2H), 4.12-4.06 (m, 1H), 3.84-3.72 (m, 5H), 3.30-3.22 (m, 2H), 2.74 (s, 3H). LRMS (ESI): 380.0/382.0 [M+H]$^+$.

Example 17

3-(Aminomethyl)-4-(2,4-dichlorophenyl)-2-methyl-6-phenyl-7,8-dihydro-1,6-naphthyridin-5(6H)-one TFA salt

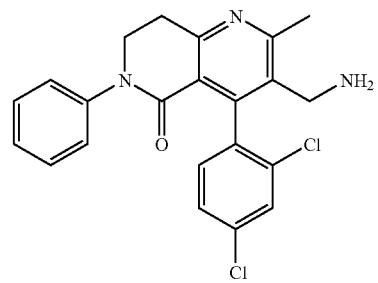

A mixture of Example 2D (126 mg, 0.38 mmol), iodobenzene (85 g, 0.42 mmol), copper iodide (16 mg, 0.08 mmol), N,N-dimethylethylenediamine (7 mg, 0.08 mmol) and Cs$_2$CO$_3$ (248 mg, 0.76 mmol) in 4 mL of MeOH was irradiated in a sealed tube in a microwave reactor at 100° C. for 4 h. The reaction was filtered and concentrated, the residue was purified by flash chromatography (elution with 0-10% MeOH/CH$_2$Cl$_2$) to afford an oil, which then was dissolved in 10 mL of 2M NH3 in MeOH and hydrogenated under 55 psi in presence of wet RaNi (~60 mg, Grade 2400) overnight. The mixture was filtered through Celite and concentrated, the residue was purified by prep HPLC (Phenomenex, 10 min gradient, 20 to 100% B) and lyophilized to dryness overnight to afford 14 mg (8% for 2 steps) of Example 17 as a TFA salt. $^1$H NMR (500 MHz, CDCl$_3$) δ7.58 (d, 1H, J=2.2 Hz), 7.42-7.22 (overlapping m, 7H), 4.09 and 3.82 (ABq, 2H, J$_{AB}$=14.6 Hz), 4.08-3.98 (m, 2H), 3.42-3.35 (m, 2H), 2.78 (s, 3H). LRMS (ESI): 412.0/414.0 [M+H]$^+$.

Example 18

3-(Aminomethyl)-4-(2,4-dichlorophenyl)-6-(2-methoxyphenyl)-2-methyl-7,8-dihydro-1,6-naphthyridin-5(6H)-one TFA Salt

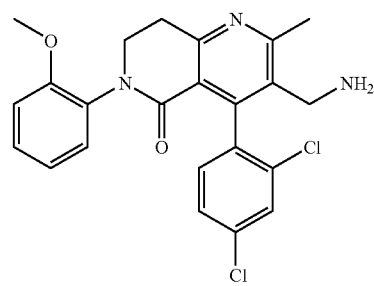

Example 18 was prepared from Example 2D using the same method described above for Example 17 with the exception that iodobenzene was replaced with 2-iodoanisole. $^1$H NMR (500 MHz, CDCl$_3$) δ7.58 (d, 1H, J=2.2 Hz), 7.43 (dd, 1H, J=8.2, 2.2 Hz), 7.32-7.28 (m, 1H), 7.23 (d, 1H, J=8.3 Hz), 7.18-7.14 (m, 1H), 7.06 (d, 1H, J=8.2 Hz), 6.98-6.93 (m, 1H), 4.10 (part of ABq, 1H, J$_{AB}$=14.3 Hz), 3.90-3.78 (m, 3H), 3.81 (s, 3H), 3.43-3.35 (m, 2H), 2.88 (s, 3H). LRMS (ESI): 442.3/444.3 [M+H]$^+$.

Example 19

3-(Aminomethyl)-4-(2,4-dichlorophenyl)-2-methyl-1,6-naphthyridine-5,7(6H,8H)-dione TFA Salt

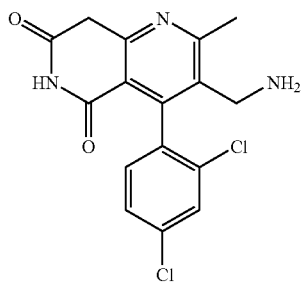

Example 19A

Methyl 5-cyano-4-(2,4-dichlorophenyl)-2-(2-methoxy-2-oxoethyl)-6-methyl-1,4-dihydropyridine-3-carboxylate

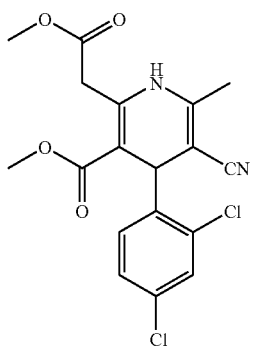

A solution 2,4-dichlorobenzaldehyde (411 mg, 2.35 mmol), 3-aminocrotonitrile (193 mg, 2.35 mmol), dimethyl 3-oxaglutarate (410 mg, 2.35 mmol), piperidine (12 mg, 0.14 mmol), and acetic acid (9 mg, 0.14 mmol) in methanol (5 mL) was stirred at 60° C. for 6 h. The reaction was quenched with 4M HCl in 1,4-dioxane (2.5 mL), The reaction was concentrated and purified by flash chromatography (elution with 0-15% EtOAc/hexane) to afford 407 mg (44%) of Example 19A as an oil. LRMS (ESI): 395.2/397.2 [M+H]$^+$.

Example 19B

Methyl 5-cyano-4-(2,4-dichlorophenyl)-2-(2-methoxy-2-oxoethyl)-6-methylnicotinate

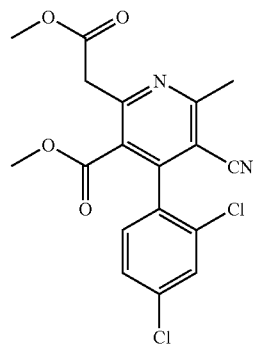

A mixture of Example 19A (407 mg, 87 mmol) and MnO$_2$ in 10 mL of CH$_2$Cl$_2$ was irradiated in a sealed tube in a microwave reactor at 100° C. for 1 h and 120° C. for 3 h. The reaction was filtered through Celite, concentrated and purified by flash chromatography (elution with 0-40% EtOAc/hexane) to afford 288 mg (71%) of Example 19B as an oil. $^1$H NMR (500 MHz, CD$_3$OD) δ 7.54 (d, 1H, J=1.7), 7.38 (dd, 1H, J=8.3, 2.2), 7.17 (d, 1H, J=8.3), 4.15 (ABq, 2H), 3.72 (s, 3H), 3.57 (s, 3H), 2.85 (s, 3H). LRMS (ESI): 393.3/395.3 [M+H]$^+$.

Example 19

3-(Aminomethyl)-4-(2,4-dichlorophenyl)-2-methyl-1,6-naphthyridine-5,7(6H,8H)-dione TFA salt

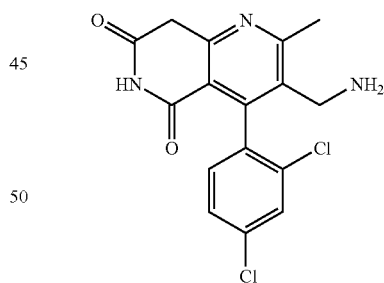

A suspension of Example 19B (120 mg, 0.31 mmol) in 5 mL of ammonium hydroxide/MeOH (1:1) was irradiated in a sealed tube in a microwave reactor at 150° C. for 60 min. The reaction was concentrated in vacuo, the residue was dissolved in 10 mL of MeOH and hydrogenated under 60 psi with ~200 mg wet RaNi (Grade 2400) overnight. The mixture was filtered through Celite and concentrated, the residue was purified by prep HPLC (Phenomenex, 10 min gradient, 20 to 100% B) and lyophilized to dryness overnight to afford 13 mg (12% for 2 steps) of Example 19 as a TFA salt. $^1$H NMR (500 MHz, CD$_3$OD) δ7.66 (d, 1H, J=2.2 Hz), 7.50 (dd, 1H, J=8.3, 1.7), 7.21 (d, 1H, J=8.3), 3.90 and 3.59 (ABq, 2H, $J_{AB}$=14.8 Hz), 3.35-3.25 (m, 2H), 2.63 (s, 3H). (ESI): 350.0/352.0 [M+H]$^+$.

Biological Activity Data

The DPP4 inhibitory activity data of the compounds of Examples 1 to 6 and 8 to 19 are obtained using the assay described herein in the DPP4-inhibition assays section are set out below.

| Example | DPP4 Ki (nM) |
|---|---|
| 1 | 6.90 |
| 2 | 2.01 |
| 3 | 37.8 |
| 4 | 39.7 |
| 5 | >100 |
| 6 | 3.44 |
| 7 | Not tested |
| 8 | 3.82 |
| 9 | 3.50 |

| Example | DPP4 Ki (nM) |
|---|---|
| 10 | 3.87 |
| 11 | 49.2 |
| 12 | 4.43 |
| 13 | 7.72 |
| 14 | 5.91 |
| 15 | 5.39 |
| 16 | 18.0 |
| 17 | 5.00 |
| 18 | 2.28 |
| 19 | 9.35 |

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A compound of the structure

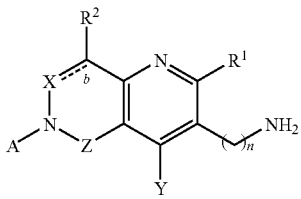

wherein
b is a single or double bond;
n is 1 or 2;
$R^1$ is selected from the group consisting of hydrogen (H), halogen, $CF_3$, cyano (CN), amino, substituted amino, alkyl, alkenyl, alkynyl, cycloalkyl, bicycloalkyl, cycloalkenyl, aryl, heteroaryl, and cycloheteroalkyl, wherein any such functional group may optionally be substituted with 1 to 3 or more substituents selected from the group consisting of hydrogen, halo, allyl, polyhaloalkyl, alkoxy, aryl, haloalkoxy, polyhaloalkoxy, alkoxycarbonyl, alkenyl, alkynyl, cycloalkyl, bicycloalkyl, cycloalkylalkyl, polycycloalkyl, heteroarylamino, arylamino, cycloheteroalkyl, heteroaryl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, arylalkylthio, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl and sulfonamido;
X is selected from the group consisting of C=O, C=S, $CHR^3$, or $CR^3$;
$R^2$ and $R^3$ are independently selected from the group consisting of hydrogen, alkyl and aryl;
Z is selected from the group consisting of C=O, C=S, and $CHR^4$;
$R^4$ is selected from the group consisting of hydrogen, alkyl and aryl;
A is selected from the group consisting of hydrogen (H), alkyl, alkenyl, alkynyl, cycloalkyl, bicycloalkyl, cycloalkenyl, aryl, heteroaryl, cycloheteroalkyl, $O—R_1$, cyano, amino, —C(O)—OH, —C(O)—$NR^6R^7$, —C(O)—$OR^6$, $S(O)_m$—$R^6$, $S(O)_2NR^6R^7$, —$NR^6R^7$, —$NR^6$—$C(O)R^7$ and —$NR^6$—$SO_2R^7$, wherein any such functional group may optionally be substituted with one to three or more substituents selected from the group consisting of hydrogen, halo, alkyl, polyhaloalkyl, alkoxy, aryl, haloalkoxy, polyhaloalkoxy, alkoxycarbonyl, alkenyl, alkynyl, cycloalkyl, bicycloalkyl, cycloalkylalkyl, polycycloalkyl, heteroarylamino, arylamino, cycloheteroalkyl, heteroaryl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, arylalkylthio, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl;
m is 0, 1 or 2;
$R_1$ is selected from the group consisting of hydrogen, alkyl, and aryl;
$R^6$ and $R^7$ are
(i) each independently selected from the group consisting of hydrogen (H), alkyl, alkenyl, alkynyl, cycloalkyl, bicycloalkyl, cycloalkenyl, aryl, heteroaryl, and cycloheteroalkyl, wherein either functional group may optionally be substituted with one to three or more substituents selected from the group consisting of hydrogen, halo, alkyl, polyhaloalkyl, alkoxy, aryl, haloalkoxy, polyhaloalkoxy, alkoxycarbonyl, alkenyl, alkynyl, cycloalkyl, bicycloalkyl, cycloalkylalkyl, polycycloalkyl, heteroarylamino, arylamino, cycloheteroalkyl, heteroaryl, cycloheteroalkylalkyl, hydroxy, hydroxyalkyl, nitro, cyano, amino, substituted amino, alkylamino, dialkylamino, thiol, alkylthio, arylalkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl; or
(ii) $R^6$ and $R^7$ in $NR^6R^7$ may be taken together to form a 5- or 6-membered saturated or partially unsaturated ring system selected from the group consisting of cycloheteroalkyl and heteroaryl; wherein such ring system may optionally be substituted with one to three or more substituents selected from the group consisting of hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl; and
Y is selected from the group consisting of aryl and heteroaryl, wherein said aryl or heteroaryl may optionally be substituted with one to three or more substituents selected from the group consisting of hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido and sulfonyl; or
a pharmaceutically acceptable salt thereof, and all stereoisomers thereof.

2. The compound according to claim 1, wherein Z is C=O and X is $CH_2$ or C=O.

3. The compound according to claim 1, wherein $R^1$ is alkyl.

4. The compound according to claim 1, wherein Y is aryl.

5. The compound according to claim 1, wherein the aryl is phenyl or phenyl substituted with one or more halos.

6. The compound according to claim 1, wherein n is 1.

7. The compound according to claim 1, wherein b is a single bond.

8. The compound as defined in claim 1 wherein n is 1;

R¹ is alkyl;

R² is H;

Z is C=O;

X is CH₂ or C=O;

Y is aryl; and

A is H, alkylcarbonylalkyl, aminocarbonylalkyl, alkylaminocarbonylalkyl, dialkylaminocarbonylalkyl, heterocyclocarbonylalkyl, alkyl, alkoxyalkyl, hydroxyalkyl, aryl, or alkoxyaryl.

9. The compound as defined in claim 1 wherein b is a single bond;

R¹ is methyl;

X is CH₂ or C=O;

R² is H;

Z is C=O;

Y is phenyl, halophenyl, or dihalophenyl;

A is H, i-propylcarbonylmethyl, aminocarbonylmethyl, methylaminocarbonylmethyl, diethylaminocarbonylmethyl, pyrrolidino-carbonylmethyl, piperidinocarbonyl, 2-oxo-1,4'-bipiperidinylcarbonylmethyl, morpholinylcarbonylmethyl, methyl, tetrahydrofuranylmethyl, methoxyethyl, hydroxyethyl, phenyl, or methoxyphenyl.

10. The compound according to claim 1 selected from the group consisting of:

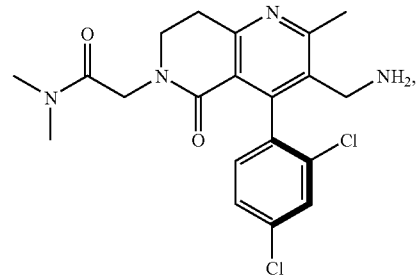

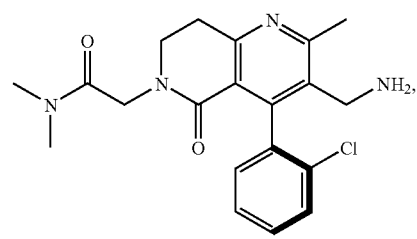

-continued

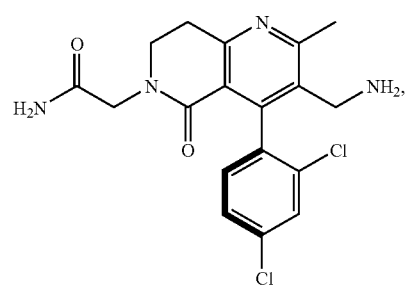

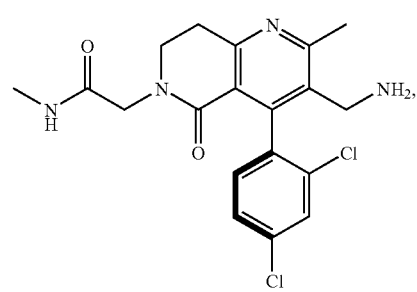

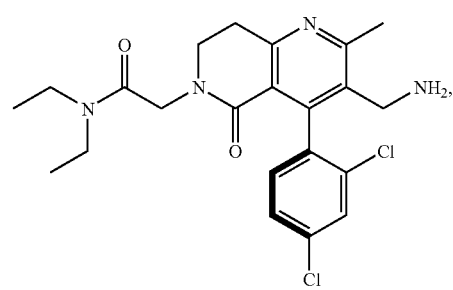

65

66

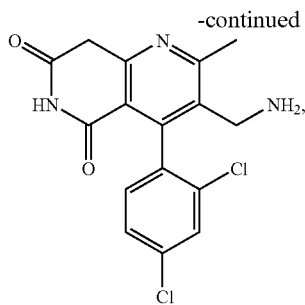

or a pharmaceutically acceptable salt thereof.

11. The compound according to claim 1 having the structure

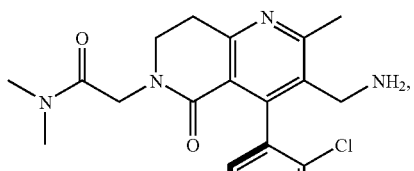

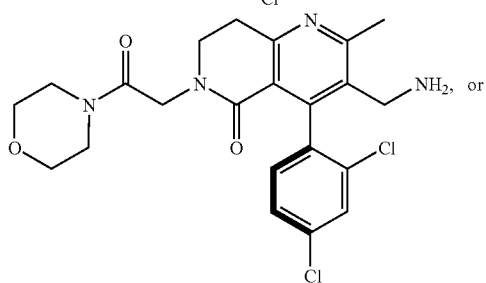

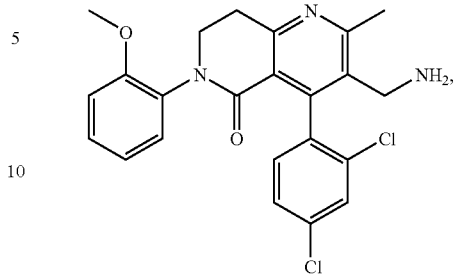

or a pharmaceutically acceptable salt thereof.

12. A pharmaceutical composition, comprising:
   at least one compound according to claim 1 alone or in combination with at least one additional therapeutic agent; and
   at least one pharmaceutically acceptable diluent or carrier.

13. A pharmaceutical combination, comprising:
   at least compound according to claim 1; and
   at least one additional therapeutic agent,
   wherein the additional therapeutic agent may be administered before the compound according to claim 1, concurrently with the compound according to claim 1 or after the compound according to claim 1.

* * * * *

UNITED STATES PATENT AND TRADEMARK OFFICE
CERTIFICATE OF CORRECTION

PATENT NO.       : 7,723,355 B2
APPLICATION NO.  : 11/941181
DATED            : May 25, 2010
INVENTOR(S)      : John M. Fevig et al.

It is certified that error appears in the above-identified patent and that said Letters Patent is hereby corrected as shown below:

On the Title Page:

Item (56), References Cited, under OTHER PUBLICATIONS:

Column 2, Bandhari, A. et al. reference, change "Bandhari" to -- Bhandari --.

The reference should read:

-- Bhandari, A. et al., "Solid-Phase Synthesis of Pyrrolo[3,4-b]pyridines and related pyridine-fused Heterocycles", Synthesis, No. 11, pp. 1951-1960, 1999. --.

In the Claims:

Claim 1:

Column 61, line 22, change "allyl" to -- alkyl --.

Signed and Sealed this
Eighth Day of November, 2011

David J. Kappos
*Director of the United States Patent and Trademark Office*

SEQUENCE LISTING

<160> NUMBER OF SEQ ID NOS: 4

<210> SEQ ID NO 1
<211> LENGTH: 18
<212> TYPE: DNA
<213> ORGANISM: Homo sapiens

<400> SEQUENCE: 1
acgccgacga tgaagaca                18

<210> SEQ ID NO 2
<211> LENGTH: 20
<212> TYPE: DNA
<213> ORGANISM: Homo sapiens

<400> SEQUENCE: 2
aggtaaagag aaacattgtt              20

<210> SEQ ID NO 3
<211> LENGTH: 19
<212> TYPE: DNA
<213> ORGANISM: Homo sapiens

<400> SEQUENCE: 3
ggtaccagcg cagaggctt               19

<210> SEQ ID NO 4
<211> LENGTH: 27
<212> TYPE: DNA
<213> ORGANISM: Homo sapiens

<400> SEQUENCE: 4
ctcgagctaa ggtaaagaga aacattg       27